(12) United States Patent
Dessein et al.

(10) Patent No.: US 9,297,044 B2
(45) Date of Patent: Mar. 29, 2016

(54) FIBROSIS SUSCEPTIBILITY GENE AND USES THEREOF

(75) Inventors: Alain Dessein, Marseilles (FR); Violaine Arnaud, Marseilles (FR); Christophe Chevillard, Aubagne (FR)

(73) Assignee: Universite D'Aix-Marseille, Marseilles (FR)

( * ) Notice: Subject to any disclaimer, the term of this patent is extended or adjusted under 35 U.S.C. 154(b) by 0 days.

(21) Appl. No.: 13/201,520

(22) PCT Filed: Feb. 18, 2010

(86) PCT No.: PCT/EP2010/052048
§ 371 (c)(1),
(2), (4) Date: Aug. 15, 2011

(87) PCT Pub. No.: WO2010/094740
PCT Pub. Date: Aug. 26, 2010

(65) Prior Publication Data
US 2012/0135403 A1 May 31, 2012

(30) Foreign Application Priority Data
Feb. 19, 2009 (EP) ..................................... 09305159

(51) Int. Cl.
*C12Q 1/68* (2006.01)
(52) U.S. Cl.
CPC ........ *C12Q 1/6883* (2013.01); *C12Q 2600/136* (2013.01); *C12Q 2600/156* (2013.01); *C12Q 2600/172* (2013.01)
(58) Field of Classification Search
None
See application file for complete search history.

(56) References Cited

U.S. PATENT DOCUMENTS

| 2003/0092019 A1* | 5/2003 | Meyer et al. ....................... 435/6 |
| 2013/0203054 A1 | 8/2013 | Dessein et al. |
| 2014/0295427 A1 | 10/2014 | Dessein et al. |

FOREIGN PATENT DOCUMENTS

| WO | WO 9511995 A1 | 5/1995 |
| WO | WO 96/38172 A1 | 12/1996 |
| WO | WO 03024308 | 3/2003 |
| WO | WO 2005/050203 A2 | 6/2005 |
| WO | WO 2008070117 | 6/2008 |

OTHER PUBLICATIONS

Fonseca et al. (NEJM Sep. 2007 vol. 357 p. 1210).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Juppner (Bone 1995 vol. 17 No. 2 Supplement 39S-42S).*
Mummidi et al (Journal of Biological Chemistry 2000 vol. 275 No. 25 pp. 18946-18961).*
Dessein et al. (JEM vol. 206 Oct. 12, 2009 p. 2321).*
San-nguanmoo et al (Journal Med Assoc Thai 2007 vol. 90 p. 251).*
Kovalenko et al. (Journal of Viral Hepatitis 2009 vol. 16 p. 612).*
Fonseca (NEJM Sep. 2007 vol. 357 p. 1210).*
RS9102373 (RS9102373 NCBI website entry ss12914243 Oct. 21, 2003).*
SS85338383 (NCBI dbSNP Website RS9402373 Entry Dec. 6, 2007).*
Syvanen (Nature Dec. 2001 vol. 2 p. 930).*
Blanton et al. "Schistosomal hepatic fibrosis and the interferon gamma receptor: a linkage analysis using single-nucleotide polymorphic markers", European Journal of Human Genetics 13:660-668, 2005.
Blom et al. "Identification of human ccn2 (connective tissue growth factor) promoter polymorphisms" 54:192-196, 2001.
Dessein et al. "Severe hepatic fibrodid in Schistosoma mansoni infection is controlled b y a major locus that is closely linked to the interferon-gamma receptor gene" American Journal of Human Genetics 65:709-721, 1999.
Fonseca et al. "A polymorphism in the CTGF promoter region associated with systemic sclerosis", The New England Journal of Medicine 357-1210-1220, 2007.
Gressner et al. "Connective tissue growth factor: a fibrogenic master switch in fibrotic liver diseases" Liver International 28:1065-1079, 2008.
Li et al. "Inhibition of connective tissue growth factor by siRNA prevents liver fibrosis in rats" The Journal of Gene Medicine 8:889-900.
Sa-Nguanmoo et al. "Analysis of connective tissue growth factor promoter polymorphism in Thai children with biliary atresia" 90:351-257, 2007.
U.S. Appl. No. 13/695,854 Office Action mailed Apr. 16, 2015.
U.S. Appl. No. 14/236,869, Dessein, et al.
Aparcio E., "IL28B SNP rs8099917 is strongly associated with pegylated interferon-alpha and ribavirin therapy treatment failure in HCV-HIV-1-coinfected patients", Antiviral Therapy, Jun. 2010 vol. 15, Supp. 2, p. A119.
Aparicio, E. et al., "IL28B SNP rs8099917 is Strongly Associated with Pegylated Interferon-a and Ribavirin Therapy Treatment Failure in HCV/HIV-1 Coinfected Patients", PLoSONE, Oct. 2010, vol. 5, Issue 10.
Backus et al., "M1785 Predictors of Sustained Virologic Response to Pegylated Interferon and Ribavirin in a National Cohort of Male HIV/HCV-Coinfected Veterans in Routine Medical Care", Gastroenterology, May 2009, vol. 136, No. 5, Suppl. 1, p. A837.
Benner et al. "Evolution, Language in functional genomics" Trends in Genetics 2001, vol. 17, pp. 414-418.

(Continued)

*Primary Examiner* — Katherine Salmon
(74) *Attorney, Agent, or Firm* — Wilson Sonsini Goodrich & Rosati

(57) ABSTRACT

The present invention discloses the identification of a fibrosis susceptibility gene locus, the CTGF gene locus, which can be used for detecting predisposition to, diagnosis and prognosis of fibrosis as well as for the screening of therapeutically active drugs. The invention resides, in particular, in a method which comprises detecting in a sample from the subject the presence of an alteration in the CTGF gene locus, the presence of said alteration being indicative of the presence or predisposition to fibrosis.

18 Claims, 3 Drawing Sheets

(56) References Cited

OTHER PUBLICATIONS

Figure 1:
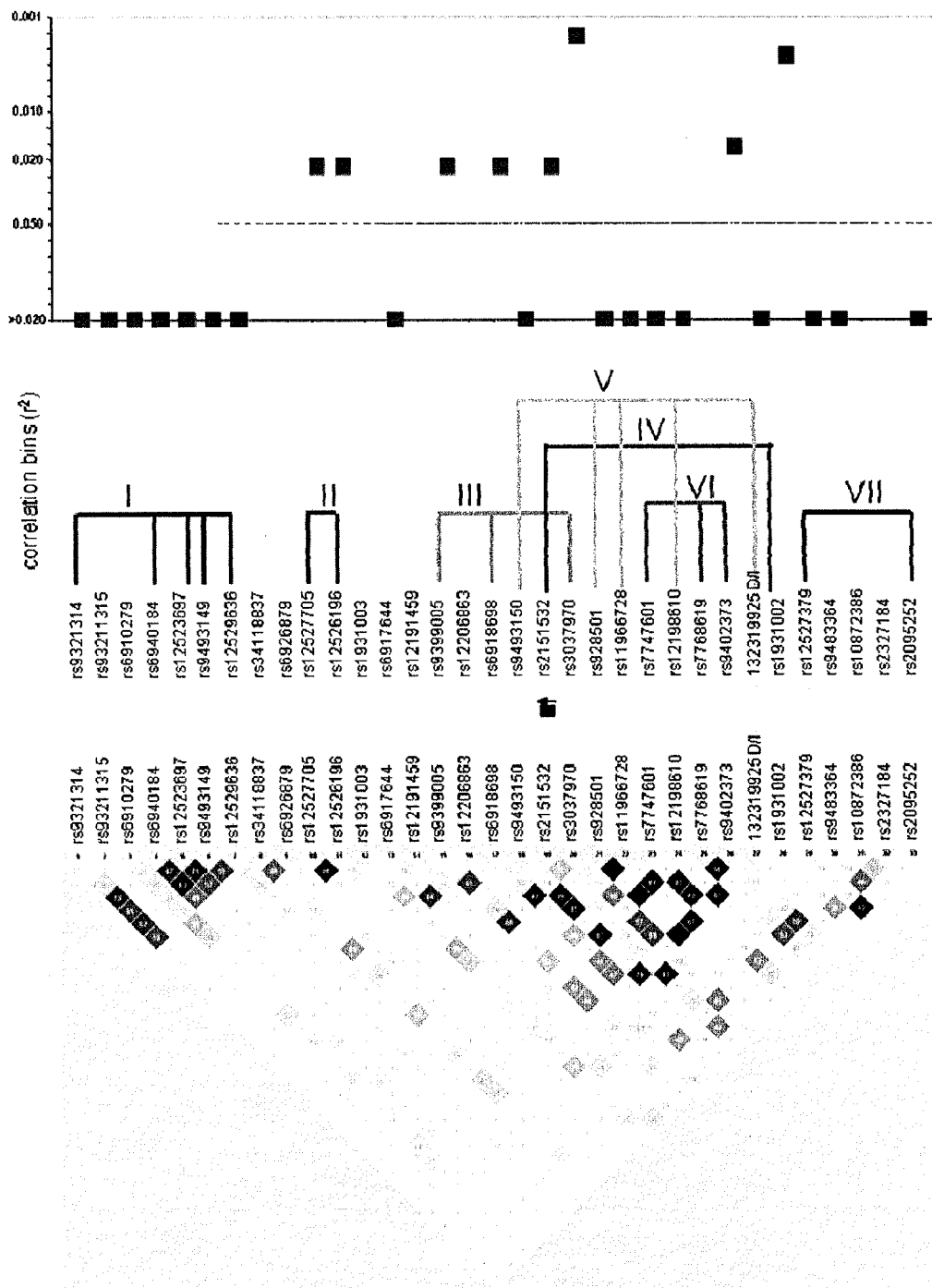

Dessein et al., "Variants of CTGF are associated with hepatic fibrosis in Chinese, Sudanese, and Brazilians infected with Schistosomes" Journal of Experimental Medicine, Oct. 2009, vol. 206, No. 11, pp. 2321-2328.

ss116721864 dbSNP (www.ncbi.nlm.nih.gov/projects/SNP/snp_ss.cgi?subsnp_id=116721864submitted Jan. 17, 2009).

Hilgenfeld et al., "From SARS to MERS: 10 years of research on highly pathogenic human coronaviruses", Antiviral Research, 2013, vol. 100, pp. 286-295.

Hora et al., "Connective tissue growth factor, steatosis and fibrosis in patients with chronic hepatitis C" Liver International 2008, vol. 28, pp. 370-376.

May et al, "How Many Species are there on Earth" Science, Sep. 16, 1988, vol. 241, pp. 1441-1449.

Oestereich et al., "Successful Treatment of advanced Ebola virus infectin with T-705 (favipiravir) in a small animal model", Antiviral Research, 2014, vol. 105, pp. 17-21.

PCT/EP2010/052048_IPRP_and_WrittenOpinion_Aug. 23, 2011.

PCT/EP2010/052048 International Search Report May 27, 2010.

PCT/EP2011/057145_IPRPandWrittenOpinioon_Nov. 6, 2012.

PCT/EP2011/057145_ISR_Jun. 27, 2011.

Phillips et al, "Liposome-Antigen-Nucleic Acid Complexes Protect Mice from Lethal Challenge with Western and Eastern Equine Encephalitis Viruses", Journal of Virology, 2014, vol. 88, pp. 1771-1780.

Posada et al., "Simple (Wrong) Models for Complex Trees: A Case from Retroviridae", Mol. Biol. Evol., 2001, vol. 18, pp. 271-275.

Schuppan et al., "Hepatitis C and liver fibrosis", Cell Death and Differentiation, Nature, Jan. 1, 2003, vol. 10, No. Supplement 1, pp. S59-S67.

Tseng et al., "Prognostic Effect of Human Leukocyte Antigen Class I and II Alleles on Chronic Hepatitis C Patients Treated by Pegylated Interferon-Alfa Plus Rivavirin in Taiwan", Hepato-Gastroenterology, May 1, 2010, vol. 57, No. 99-100, pp. 456-461.

U.S. Appl. No. 13/695,854 Non-Final Office Action Dec. 4, 2013.

U.S. Appl. No. 13/695,854 Final Office Action Jun. 24, 2014.

Kawaguchi et al., Association study of a polymorphism of the CTGF gene and susceptibility to systemic sclerosis in the Japanese population. Ann Rheum Dis, 88:1921-1924 (2009).

\* cited by examiner

SEQUENCE LISTING

```
<160> NUMBER OF SEQ ID NOS: 142

<210> SEQ ID NO 1
<211> LENGTH: 701
<212> TYPE: DNA
<213> ORGANISM: Homo sapiens
<220> FEATURE:
<221> NAME/KEY: misc_feature
<222> LOCATION: (501)..(501)
<223> OTHER INFORMATION: w=A/T

<400> SEQUENCE: 1
cagatctcag ttcatctctt tacgattggg agagtctgga agaaaaagat ctatctatat      60
taatagagat tcttagagg tgcaaatttt ccctcacaaa gaacaacttt gcggggccat     120
ttcaaaatat ggcaaagaaa catgttttgg ggaaatgcac tttttaattg atgtatattg     180
ttccattata taaatattct atactctatc aattttctg tttacagaat tcagattttt      240
gctttcagtt tttggatgga tgaaactgct ttgagaattt tgtatgtctt ttgctcactt     300
ctcttgaata tataccaaag actaaaagtt attgtagtta tctaaattat acatgttaac     360
ttgctgacaa aaattgtgtt agaatttgtt gacctaatgt aaaagttta tattcttgcg      420 atgcaaattc taattaatca atggtgctcc tcatttctta ctaactcttc tttgactctc     480
ttttaaacat gtaatataga wgatgggtct acatgtctat tgctttgaat cctatattta     540
ggtttggaat ctgacagtat tttaagaata tatttactt tgtttatttt gttcttagtc     600
ttagaaacag tctatatata attagtatga ttcatgaggt aaggaatagt tatacagagg     660
aaaatcgttc accattttat ttatggtata gagaaataga g                         701

<210> SEQ ID NO 2
<211> LENGTH: 501
<212> TYPE: DNA
<213> ORGANISM: Homo sapiens
<220> FEATURE:
<221> NAME/KEY: misc_feature
<222> LOCATION: (251)..(251)
<223> OTHER INFORMATION: Y=C/T

<400> SEQUENCE: 2
```

```
ctctcttta aacatgtaat atagaagatg ggtctacatg tctattgctt tgaatcctat    60
atttaggttt ggaatctgac agtattttaa gaatatattt tactttgttt attttgttct  120
tagtcttaga aacagtctat atataattag tatgattcat gaggtaagga atagttatac  180
agaggaaaat cgttcaccat tttatttatg gtatagagaa atagagtaaa agacaacact  240
gaatatacaa ygaatatggg cattccctag agattcgatg tgtgttgcat gtactcctag  300
gcacgtggct aattaagata tagtggtttg aatagctaag ttatttactt atttatgtat  360
tgtgtattgt ttcatctaaa tgaaaatcat aaaatacttg aacactttt gacatattcc   420 ttgctgtttt tttaatgaga tggaaatttg tttttaaaa aatctctttc ttataatgta   480
tgttcatttc aaaaaatttg a                                             501
```

`<210>` SEQ ID NO 3
`<211>` LENGTH: 401
`<212>` TYPE: DNA
`<213>` ORGANISM: Homo sapiens
`<220>` FEATURE:
`<221>` NAME/KEY: misc_feature
`<222>` LOCATION: (201)..(201)
`<223>` OTHER INFORMATION: Y=C/T

`<400>` SEQUENCE: 3

```
aacggaatta tacaaaacaa gacttatgaa atagctccat ttaaatgagg atttcatttc    60
ataattttca gatttaacag taaggtaatg aagttcagaa acagacctag agcataaaat  120
ttttaaaaaa tgtaaacatt ttccacgtgc aaggcacata gactagtttg tgatgtgaag  180
ggttggaaac taacctataa yggccagaga ggtacaaatg ccaaaggac caagtgtaat    240 acaacagggt taatggagac tgaagtaatc tagagagaat tgaatttaaa gtgtctataa   300
agttctgtga agataacaaa aaaaatggct gtatagtcaa tgtggtgtgt atgcctgcaa  360
gtctgtgata cttgattcag tgtgaagtat gtttacataa a                      401
```

`<210>` SEQ ID NO 4
`<211>` LENGTH: 601
`<212>` TYPE: DNA
`<213>` ORGANISM: Homo sapiens
`<220>` FEATURE:
`<221>` NAME/KEY: misc_feature
`<222>` LOCATION: (301)..(301)
`<223>` OTHER INFORMATION: S=C/G

`<400>` SEQUENCE: 4

```
cccccaacc cttagcaatg atttgcgttt tagaggctat aggctcttga aactctccaa     60
agagtagaaa aggagtgagt tgcttttaac catttgaaat cctcaagatg cctacctgta  120
aaaccctgaa ttctatattt gagatttgat catttgtcac ttgaggtaac ggttttggga  180
caagaaagag aacaaagacg cgtgtgactc aggatgcagt ctcctggggc agatttccaa  240
aactcttgct tagttttctc ttaatatatg taggagtttt atataggcaa ggacaaggga  300
sgagtggcca tcaatgtttc cagaaaaagg gatccattgt tctatcagag caaatgattc  360
tgtgttgggt aggtagggc tctgggtgtc agggtgggaa cactgggatg caagggggt    420 tcacctagga gcatttaaac acagcttcac tagggtcttt gagaaatgag tgcattttct  480
tatattaaaa cctataatct tcaaatgtgg attggatttg gtttgtcttg ttaaaataag  540
aagtctgatt ccattacaag agcagtgtac cctgttgtat ctggatataa actaagattg  600
a                                                                  601
```

<210> SEQ ID NO 5
<211> LENGTH: 984
<212> TYPE: DNA
<213> ORGANISM: Homo sapiens
<220> FEATURE:
<221> NAME/KEY: misc_recomb/insertion_seq
<222> LOCATION: (489)..(490)
<223> OTHER INFORMATION: with or without insertion of TAAAA between
      position 489 and 490

<400> SEQUENCE: 5
gtactgggtt atagttagat ggcctaggtt gtattcttgg aactgccttt cgcagatctc    60
agggaagtca cacgtaggag ccatattccc atttctgttt aaaaaatgaa agtaatcata   120
atttttttaa tttaataggg ttcagtgagg gctgagtaga tgaaaattcc agggaattgg   180
tgctttattt ttttcagatt ttcttgattt tttttcaatc tctgtgtata ataagtatat   240
taccattctg ctctgttgtt aaaaatgtca aaagaaagaa tttggtttta ctataaaatt   300
ctcatagtcc ctcgaagtct caaaaaaatc tatagtcagt tccaaataga tgattttaat   360
gttgcttaag aggaaataag catattgaaa tatatagaac atatgaaatc tcaggaaaga   420
aaaagtttct gtgcattatc aggttagatt gaggctttat gatcaaaact cttttttgaag  480 gagttaaaag actattatta agagagtgac acagagacag acagacacat acatgcacac   540
acacccagag agagagagaa tgagagaaga cacccaagac attcacagac tcagaagtat   600 gttttttattg tgatatggac catcaaatgc caggaaactc aaagggaaag gctgatactc   660
catccataat tcatgccatg ggatctgaat tcttgcacta ttatcaatga ctcagcaaat    720
gtttgtgtgt gcctgggcgg taaagtggga aatagtggct tcttataact tcatccaact   780
ttgacttacc ccagccccctt tgattgacag caggtcagag ttgggagaaa aagatctttg   840
aatttgtgtg caaaatggtt aagatgcact aattttgact tgtaagcaag tatttatcta   900
gcaaatgctt tttagagagc attttttcct cgtggtaaaa tgaggaatta actaagctgg   960
ccactgagtc ctgtttacca agct                                         984

<210> SEQ ID NO 6
<211> LENGTH: 586
<212> TYPE: DNA
<213> ORGANISM: Homo sapiens
<220> FEATURE:
<221> NAME/KEY: misc_feature
<222> LOCATION: (228)..(228)
<223> OTHER INFORMATION: R=A/G

<400> SEQUENCE: 6
aaattaaaca atgcattagt tgactttac ttcaaatctg atgatgtcag gattttaaat    60
agaatgtggt ttttcttcat atgtggtgaa agttctgact tagaagataa gatacccttct  120 caaaaagcct tatccaggtg ctcagatttt aatatatgat tcccataggc atggttattt   180
aaagatttac acacaggaaa atagtttaga aactcttttgg atgattcraa caacttggtt  240
tttagcattc tagaacatac tggctaccaa gtttgctttt aatttgaaaa cttgtcacca   300
tcatggtagc acagttcaca ttacaaaatg aaatgaaaga aaactgtcaa cccaaatata   360
tgtaaagtgt taaagtctgt agcatcacat taagtaaaat accaccttgg tttccaagaa   420
atacaaatct aaagaaaatg tgatggacac aagcaatcat aattttttgg ttgtttcttt   480
atcatttgca taccatattc ttattagtga taagttacac attttcact gaagaaagga    540 agactgttag gaactcccta actctcccca tcctccacaa atcaat                 586

<210> SEQ ID NO 7
<211> LENGTH: 501
<212> TYPE: DNA
<213> ORGANISM: Homo sapiens
<220> FEATURE:
<221> NAME/KEY: misc_feature
<222> LOCATION: (251)..(251)
<223> OTHER INFORMATION: Y=C/T

<400> SEQUENCE: 7

| | | | | | |
|---|---|---|---|---|---|
| tttgacattt | ttaacaacag | agcagaatgg | taatatactt | attatacaca | gagattgaaa | 60 |
| aaaaatcaag | aaaatctgaa | aaaaataaag | caccaattcc | ctggaatttt | catctactca | 120 |
| gccctcactg | aaccctatta | aattaaaaaa | attatgatta | ctttcatttt | ttaaacagaa | 180 |
| atgggaatat | ggctcctacg | tgtgacttcc | ctgagatctg | cgaaaggcag | ttccaagaat | 240 |
| acaacctagg | ycatctaact | ataacccagt | acaacaattt | atccctcca | tgaatgagtc | 300 |
| tccctgctgc | aggcatgaag | atggtggtag | ctttcagact | ctcctgagga | ttcagaaatt | 360 |
| ccccaaccct | tctcccacct | acctcactct | gcaagctagg | agagctcacc | accaagccca | 420 |
| catcccacct | taggtgagac | tcgcactgca | catccctacc | cttccccagc | caccacacct | 480 |
| ttccaaccat | tagaggtaga | t | | | | 501 |

<210> SEQ ID NO 8
<211> LENGTH: 817
<212> TYPE: DNA
<213> ORGANISM: Homo sapiens
<220> FEATURE:
<221> NAME/KEY: misc_feature
<222> LOCATION: (317)..(317)
<223> OTHER INFORMATION: S=C/G

<400> SEQUENCE: 8

| | | | | | |
|---|---|---|---|---|---|
| cccatcattc | atccctggaa | atgtgctccc | acctctagcc | aagaggcctg | aggtcccttc | 60 |
| tcacaacttc | aaactccctg | gaataccatt | aggtggagcc | taggggactg | gctaggaggt | 120 |
| gaaggtgtga | gctccatacc | tgccatttgc | ttgccagtga | cctcagggaa | gacacctact | 180 |
| ctctctgagc | ctgaaatttc | ccacctgttc | acagttaatg | tgcagctcaa | ggagacaata | 240 |
| tttatgaaag | cactttcata | aaggtattag | agttttaaaa | ttgcccttct | cttccattct | 300 |
| tcagtggctc | tcaaaastaa | gcccaactca | gattgactgt | aaaagcctgt | cacagtttga | 360 |
| ttttataaca | gtgtccagct | ctgcatgggt | tttagagtgt | taaaactagg | tgagagctca | 420 |
| gagaaaatca | aatcctacct | cttatttatt | tatttatttt | attagattag | atattcagga | 480 |
| ttgatagaga | catttaacaa | atgaaaactt | tttttctttt | tgaaataggg | tctggctctg | 540 |
| tctcccaggg | tggaatgtag | tgccatgatc | ttggctcact | gcaacctctg | cctcctgggc | 600 |
| tcaagtgatc | ttcctgcctc | agcctcccaa | gtagctggga | tagctgggac | tacaggtgtg | 660 |
| caccaccata | tccagctaat | taaaagaatt | tttttttttt | ttttgtaga | gatgggttt | 720 |
| tgccatgttg | cccaggctgg | tctcgaactc | ctgagctcaa | gagatcagcc | catctcagcc | 780 |
| tcccaaagtg | ctgggattac | aggcgtaagc | ccctgcg | | | 817 |

<210> SEQ ID NO 9
<211> LENGTH: 601
<212> TYPE: DNA
<213> ORGANISM: Homo sapiens
<220> FEATURE:
<221> NAME/KEY: misc_feature
<222> LOCATION: (301)..(301)
<223> OTHER INFORMATION: R=A/G

<400> SEQUENCE: 9

```
ataattgtat cattcactga taagctaccc ttagggataa atatcatgac agagtctggg     60
acaaaccatc agcactgaag caatgtctac tatcaacata ggttttcac gagtatcccc    120
taataaacat gtcctgccat gttattgata tttattttat gaacttgcct taactgaaaa   180
tgcactttcc tcaaactgaa tatgctttgc ctttcaggtt tacagctttc tccctctctc   240
ctttaaccat ggaaggattt gatttgaatc ataactagtt tcatgttgtt aatggaatgc   300
ratttgtcat aactacacat ggcagagaga gagggttgtc taggaatggt ggggttatga   360
tgagggaatt ttcttattga cctgcacatg tgtgtgaaag ttaacaacta caggattaca   420
tttcatataa ccattgactt gctcatgtct ggaaataata tcactattaa gctatttctc   480
atatacagat gataaaaact tatttgtcc aattgaatct tttgtggcat ttcatcatt    540
tctaacgtct ctatgttggt tcttcttgat tgtggttttc cctgctgttt ccgtatttga   600
c                                                                   601
```

<210> SEQ ID NO 10
<211> LENGTH: 1001
<212> TYPE: DNA
<213> ORGANISM: Homo sapiens
<220> FEATURE:
<221> NAME/KEY: misc_feature
<222> LOCATION: (501)..(501)
<223> OTHER INFORMATION: R=A/G

<400> SEQUENCE: 10

```
tgagaggcta tgagtggggt cagctttacc caaagtacat gggctgaaac ttgggggaat    60
aatccaccag agcaaagatc agcaattttt tttcttgaaa agggccccat agtaaatatt   120
tttagccttt gtgggctata cagtctgtca ctcaattctg ccactgtagc tcaaaagcag   180
ccatggatac tacattttt taaaaaaggg catgaccgtg taccaagaaa actttgttta    240
caaaatcaga gagcaggcca gattcagatg acaggccaga gtttgccaac ccctgcacta   300
gagcgagatt aagtacagtt atcagactgg aagtcaggct ataaaaataa gcaacagatg   360
tccaccacat gcatagaata atatagatat ccctgcttct ctgggtcttt agcttttctc   420
tctctttgta ataagagtca taacagatga ctttaggagg ctcttttct tccaaagttc    480
tcctgacctc aaattaaaat rgtctactga gagtccaggt ggtggctttt gcaaatgctt   540
gggatccagg aggaaaggtg acagccttca tggtagcaag cctatagaca gtagcagccc   600
cagaatcaaa taatttgctt ctagatataa cactttcaca tgctaaaata taaacctct    660
ctcctcagaa aaactaatct acttcttccc tagtctttcc aatgccagat aacagcacca   720
cagtttgtcc attcatttag gcaaaaagct ggggtgatat actcatttc ctgttaatat     780
ccctcagcca acctatcagc aagtcccatg tgcagaatat gcactgaatc tgaccactcc   840
atctacgtcc accaacacag ctcccacccg tgtcaccatg cgcctctcct ggacttctcc   900
agtagcctcc ccagtctccc tcctccctct tgctcctcta ctgtcctttc tcaattcagc   960
agccagaatg atctttctaa catctaaatc ctcccgtgac c                      1001
```

<210> SEQ ID NO 11
<211> LENGTH: 861
<212> TYPE: DNA
<213> ORGANISM: Homo sapiens
<220> FEATURE:
<221> NAME/KEY: misc_feature
<222> LOCATION: (361)..(361)

<223> OTHER INFORMATION: W=A/T

<400> SEQUENCE: 11

| | |
|---|---|
| agttctcctg acctcaaatt aaaatggtct actgagagtc caggtggtgg cttttgcaaa | 60 |
| tgcttgggat ccaggaggaa aggtgacagc cttcatggta gcaagcctat agacagtagc | 120 |
| agccccagaa tcaaataatt tgcttctaga tataacactt tcacatgcta aaatataaaa | 180 |
| cctctctcct cagaaaaact aatctacttc ttccctagtc tttccaatgc cagataacag | 240 |
| caccacagtt tgtccattca tttaggcaaa aagctggggt gatatactca ttttcctgtt | 300 |
| aatatccctc agccaaccta tcagcaagtc ccatgtgcag aatatgcact gaatctgacc | 360 |
| wctccatcta cgtccaccaa cacagctccc accgtgtca ccatgcgcct ctcctggact | 420 |
| tctccagtag cctccccagt ctccctcctc ctcttgctc ctctactgtc ctttctcaat | 480 |
| tcagcagcca gaatgatctt tctaacatct aaatcctccc gtgacctctc attatgctat | 540 |
| ttatttattt attgagatgg agtcttcctc tgtcacccag actggagtgc agtggcatga | 600 |
| tttcggctca ctgcaacctc tgcctcccag gttcaagcgg ttcttctacc tcagcctccc | 660 |
| tagtagctgg gactacaggc atgcatctcc acacctggct aattttttgta tttttagtag | 720 |
| agaggggtt ttaccatgtc agccaggctg gtctcaaact cctgagctca ggtgatctgc | 780 |
| cctccttggc ctcccaaagt gctgggatta caggcgtgag ccaccacgca cagcttcctt | 840 |
| atgtttaaaa ctaaacctca g | 861 |

<210> SEQ ID NO 12
<211> LENGTH: 1249
<212> TYPE: DNA
<213> ORGANISM: Homo sapiens
<220> FEATURE:
<221> NAME/KEY: misc_feature
<222> LOCATION: (973)..(973)
<223> OTHER INFORMATION: R=A/G

<400> SEQUENCE: 12

| | |
|---|---|
| aaaacctctc tcctcagaaa aactaatcta cttcttccct agtctttcca atgccagata | 60 |
| acagcaccac agtttgtcca ttcatttagg caaaaagctg ggtgatata ctcatttttcc | 120 |
| tgttaatatc cctcagccaa cctatcagca gtcccatgt gcagaatatg cactgaatct | 180 |
| gaccactcca tctacgtcca ccaacacagc tcccacccgt gtcaccatgc gcctctcctg | 240 |
| gacttctcca gtagcctccc cagtctccct cctcccctt gctcctctac tgtcctttct | 300 |
| caattcagca gccagaatga tcttctaac atctaaatcc tcccgtgacc tctcattatg | 360 |
| ctatttattt atttattgag atggagtctt cctctgtcac ccagactgga gtgcagtggc | 420 |
| atgatttcgg ctcactgcaa cctctgcctc ccaggttcaa gcggttcttc tacctcagcc | 480 |
| tccctagtag ctgggactac aggcatgcat ctccacacct ggctaatttt tgtatttttta | 540 |
| gtagagaggg ggttttacca tgtcagccag gctggtctca aactcctgag ctcaggtgat | 600 |
| ctgcccctcct tggcctccca agtgctggg attacaggcg tgagccacca cgcacagctt | 660 |
| ccttatgttt aaaactaaac ctcagcagag tttacaaggt ccctatgacc tagacttcct | 720 |
| caaccctccc agcctcatct ctgaacactg tctccttttt aactggagct gaaaggagga | 780 |
| ggaataaagt aacttcaata acaaccaga acagtgcttt caaatgtcac ttttggtgat | 840 |
| gatggaaatg ttctatatct gtgctgtcta gtatggaagc cactagccgc atgtcactac | 900 |
| tgagtgtttg aaatattgct actgtgacag agaggctgac ttttacactg tacttaattt | 960 |
| taattcattt aartgtaata gccacatttg tctatcagct actatggaca gcaaaaaact | 1020 |

```
agaatatggg caaaactgat ataaatgata aaataaagtt atgaacagta tttgttaggg    1080
catctgaaag gaaagagggc tgctaggagg ttatgggatt cagggtagta ttaaaaaatc    1140
attcaaaaag tgacttctgg gaagggcttt aaatgatgag tgaagttgac ttagatataa    1200
atatatatgt gcttatatat atacatatac acacatgcat tatgagaag               1249

<210> SEQ ID NO 13
<211> LENGTH: 2706
<212> TYPE: DNA
<213> ORGANISM: Homo sapiens
<220> FEATURE:
<221> NAME/KEY: misc_feature
<222> LOCATION: (1997)..(1997)
<223> OTHER INFORMATION: K=G/T

<400> SEQUENCE: 13
ctatatttta gagcagttat gtacgtttat gtatatctct gtgtgtatac atataaatat      60
atatatatat atgcatgctt atgtataagt gaaatgaatg acaacaatga tacaagggac     120
aggagggagg aatttggatt acttgttatt gcaaagtact tgtactatct atgaagctgt     180
acagtgttat atgaaagtga acctggctgg gccaggtgca gtggctcaag cctgtaatcc     240
cagcactttg ggaggctgaa gtgggtgcat cacaaggtca ggagctcgag accagcctgg     300
ccaatatggt gaaaccctgt ctctactaaa aatacaaaaa tgagcagggt gtggtggcag     360
gtgcctgtag tcccagctac tcaggaggct gaggcaggag aattgcttga acgcgggagg     420
cagaggttgc agtgagccga gaatgcacca ctgcactcca gcctgggtga cagagcgaga     480
ttctgtctca agaaaaaaaa aaaaagaaa gaaagtgaac ttgggtttgt tgtaaatgtg      540
tattgcaaat tctagagcaa ccgttaaaaa agttttttaaa aaagtagaat tgatatgcta     600
agaaaggaga gaaaatggaa tcatgtaaaa tgctcagtta atgccacaaa agacaaaagc     660
cctgtggaac acaagaagaa acaaagaaca agagcaacac atagaaaaca gtaacaaata     720
tggtagatgt taagccaact atatcaataa tcactgtaga tgtcagtggt ctaaatatgc     780
caattaaaag acagagcttg tcagagtata ttaaaaacac accagccgtg gtggtgcact     840
tgtgtaaccc cagctacctg ggatactgtg tgcggaggat ataaagccta ggagttcatg     900
accagcctgt acaacatagg gagaacctgt ctcaaagaaa acaaacaaa caaaaaatca     960 agacccaact aattattgtc tgtaagaaac ccatgttaaa cagattagac tctgacaaaa    1020
cacgcatagg ttaaactcta gtaaaatact ttctcccgag ggtaggccct gctaagaaga    1080
gtacccagat gtatttcaaa atggttactt tcctcctccc actgctggaa gagcaaggaa    1140
atttttctcc aatatttggg gagataaaac tccccaaaac atgtgtgggt ggagggacag    1200
ggggcccatg actgtatctg ggaccacttt ttatataaac aaatctctaa attgaagttc    1260
aaatatttga gtgttggtga aaaagaaatg gagttattct gatacttgtg actcattact    1320
attatatata ttttttgctt aaattgtctc aggtttaatt attgcgagct ccttcaagtt    1380
gtcttttcag tatgaaccta acatttttttt cagcaatttc ttacttgctg gtgccacaag    1440
tttttgcagg tttatcttgc attttctctg cctgagccat gaaatcagcc attttttccaa    1500 aaagccctag ttccttttat tggacattat taaaatttgg gttctacata tgttaattgt    1560
tctggggtgt cacagcacct aggatgatga cagctcagtt gacagaaaat acacatacag    1620
ctaagtgcat atataaaccc attctatatt tatgtctgtg tatatctata catgcattaa    1680
aaccatgagc tgtgctatgc ccaagccctc acaattactc attacttacc cattgacttg    1740
```

```
gcttgatcaa atgctagtca ggcttctccc tacaggtccc agaactttat cttattccca    1800
agcttttaag caagtgctaa gttacagaat atcttctcaa tgacttactc caagaatcca    1860
gtgaccaaag agaataaaaa tttactgtca aagccactct catgccatct gcctacctcc    1920
attcgcttgc cccactcttt cacaaacttc ctgctagccc tatttacttc tccttataaa    1980
agaaaggtct ttttctkttc gacctttaga ctttgccact tctgcaatag agtattctcc    2040
ctatttcaaa gttctcttcc ccatattgca atgcagttgg tccttgaaaa acacaggggt    2100 tagggggtgct gaccccttgt gcagttaaaa attcacgtaa aattttttgac tcaccataaa    2160 cttaactact actagccgac tgttgactgg aagctttacc aataacacaa acaatagatt    2220
aacacatatt tgtgtgttat atatatttga cactgaattc ttatagtaaa gtaagagaaa    2280
ataaaatgaa aaaatgccat taagaacatt atatggaaga gaaatatat ttattactta     2340 ttaaatggga atagatcatc agaaaggtct ttatcctcat tgtcttcatg atgggcaggc    2400
tgaggagaag agaaaagagt aggagttggt cttgctgtcc cttggcgtaa ctattattga    2460
aaaaaattca tgtataagtg gatttgtgca gttcaaaccc atgttcttca agggtcaact    2520
gtggcctttt tgaataaaat ctctatttta atctggcttt taaaaaattt gactactggt    2580
actactaatg gcaacccaat accacaggtg tttgaattaa tcagttaatt gcctttattg    2640
aaagaatgtc tatggtcttt tataatttat attttcctca agatagattt gtactgaaat    2700
aaaatc                                                              2706

<210> SEQ ID NO 14
<211> LENGTH: 701
<212> TYPE: DNA
<213> ORGANISM: Homo sapiens
<220> FEATURE:
<221> NAME/KEY: misc_feature
<222> LOCATION: (501)..(501)
<223> OTHER INFORMATION: Y=C/T

<400> SEQUENCE: 14
ttggtccttg aaaaacacag gggttagggg tgctgacccc ttgtgcagtt aaaaattcac      60
gtaaaatttt tgactcacca taaacttaac tactactagc cgactgttga ctggaagctt    120
taccaataac acaaacaata gattaacaca tatttgtgtg ttatatatat ttgacactga    180
attcttatag taaagtaaga gaaaataaaa tgaaaaaatg ccattaagaa cattatatgg    240
aagagaaaat atatttatta cttattaaat gggaatagat catcagaaag gtctttatcc    300
tcattgtctt catgatgggc aggctgagga agagagaaaa gagtaggagt tggtcttgct    360
gtcccttggc gtaactatta ttgaaaaaaa ttcatgtata agtggatttg tgcagttcaa    420
acccatgttc ttcaagggtc aactgtggcc ttttgaata aaatctctat tttaatctgg    480
cttttaaaaa atttgactac yggtactact aatggcaacc caataccaca ggtgtttgaa    540
ttaatcagtt aattgccttt attgaaagaa tgtctatggt cttttataat ttatattttc    600
ctcaagatag atttgtactg aaataaaatc taactttat taaaactgaa aaagggaaat    660
ggaggattca ttgacaatgg ggtgtttcta tctgggtaac a                       701

<210> SEQ ID NO 15
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: R=A/G
```

<400> SEQUENCE: 15

```
ggtttccata gcagcagctt ctagcagcca ctcctattgg cctgggtcct taccacaagc    60
agcacctccc tgcagatctt cctgctggtg aatgctgctc caagtgatta atgacttcca   120
ttcccctaga atctcattca gtgaatccta aaatgttcaa cttaaagga cctcaatccc    180
aaacatcttc tctacaaaac rtctggattt ctccaatagc tagagggagc atttgatttc   240
tagcagcacc cccaagccag gtctcaatag gctccttacg aagccctggg gttcagttag   300
aatgccacac tgttttttca aagtccttta ttatctccat cggctactat tcatacctcc   360
ggtagaagag tcccattgac aggtgttctg gacttcaggc t                        401
```

<210> SEQ ID NO 16
<211> LENGTH: 601
<212> TYPE: DNA
<213> ORGANISM: Homo sapiens
<220> FEATURE:
<221> NAME/KEY: misc_feature
<222> LOCATION: (301)..(301)
<223> OTHER INFORMATION: R=A/G

<400> SEQUENCE: 16

```
atgtaaacag agtcctggca aatagcccag acctcccagg gctccttaac ataagtacgc    60
aagcttgcct aataatcctg agtttaaaat tatgagtgac ataagataat cttcacactg   120
ggagtcatcg gcccaaatta cggttaaagg ttaaaaacaa acaaataaaa tgcaaaaaaa   180
aatcacatac aaaccaggct tatgttgtag aaaatatttc ctaagcccct tggatttaatg  240
tcatttttag agtttgatga tacctcccta gagagggtat aacaaatact gaacaaggat   300
racacagatc agaaagaatt tagctaggga ggaattcaga ttggggagaa aaataaggag   360
ttgggcctat tctcatttaa aaataaatcc ctctggaaag acataaaaga acattttaa    420
aaagactaaa agaatggcag tttatctttt cattttaat gctaagtgtt tctattttaa    480
agggcttcca tcccaagtat atacttggat tgaaaaatgg aaaacagtta aaaatgaaga   540
tttttaagtt caaaatgttg atcaaaattt cctgattcaa attgcttttt tgactcttgg   600
a                                                                    601
```

<210> SEQ ID NO 17
<211> LENGTH: 1001
<212> TYPE: DNA
<213> ORGANISM: Homo sapiens
<220> FEATURE:
<221> NAME/KEY: misc_feature
<222> LOCATION: (501)..(501)
<223> OTHER INFORMATION: R=A/G

<400> SEQUENCE: 17

```
tatgcaaata aatatatatg ccaataaata tatgcaaata aacaggcaga atgttctac     60
tttttacact gtatacagta ctttctcctt tttaaccttc attcagtctt agttctaaag   120
gtgagctata ttcaattctc actacagtcc ttaggttagt atctctcaga catttgtgtt   180
gtttgagctt gtttgctagt aggttcctca gcaagggctc acaggaaaaa tatgccctga   240
gttcttgtgt gttttttaaca gtttgtctgt gtccttcctg ttcattgcag cactatccac   300
gatagctaag ttatggaatc aacctaagtg tccatcaaca gatggatggg taaagaagat   360
gaggtatata tacacaatgg agtactattc attaaaaaag aagggaatcc tgtcatttgt   420
gacaacaggg atgaacctag tcattcaagg tttgatttca agaatcaagt cattcttgaa   480
```

```
aatcagtttt agaggataaa rgtttcttga ctctcatttt ctttccttaa gtatcttaaa      540
taagttattc cattttttc tgtcataaag tattgctgta aaaaaaatct aacgatgagc        600
taattttctt tttatttata aggctcatgt tcttttttgtc ttcatgttca aatagctttt     660
cccttttctt taaactccag cagttttact agaatgtgtt ttgctgttag ttgatttgtt      720
taggcacatg gcacacccctt tcaacttgtg ctttcaaata cttttttatt ctagtaaagt    780
tttttttgac ttatagcttt taggatttt ttttcttctt taagaatttc taccctccac      840
atattggatt ttctttgcct gtccacaata tttattactt tttattgcaa tatgtttatt    900 tcttcttta tatttaaact tgttttctta tctgtaagag tatattcact cttatgctcc     960
ttgtagtttg atatagttcc tttatttcta aatctctgtt g                        1001
```

<210> SEQ ID NO 18
<211> LENGTH: 601
<212> TYPE: DNA
<213> ORGANISM: Homo sapiens
<220> FEATURE:
<221> NAME/KEY: misc_feature
<222> LOCATION: (301)..(301)
<223> OTHER INFORMATION: S=C/G

<400> SEQUENCE: 18

```
tgtgtgcaga tgttgaatat ggccaataaa cctaagcata tctccatttc ttaatatagt     60
gctacttagc ttcactaaag acccaactaa ttcactgtgc tttcatttgg aatctatgtt    120
gtttagtggc ttttttgtta atacctccag ttcccatttt atataaagag agtgattcta    180
gggccatacc attttgtat tctgtaatgc cgcatcattt gacattggtg ttaccaatga   240
gtagattcct ttaagttgtt gatgcttcag agcatgggtt caagataagc atatctgttt    300
stggtgcaaa gatcggcttt agaaacaatg cattatagat ttatcatttg aaaacagcct    360
gtttaaactg atcaaatttt taaagtttca gtacagtctg ttgaaaaata gccaagaaga    420
aatataacca ctccaacttc agcatagagc atatcatctg tgcacgatta cctcgttaag   480
ccagccacat gttatagagt gtagttgcat gtcaatagtg tgaatggcca gcaaaggggt   540
gggggtgccc tctgaagctc aggaagaatt tcgtcattg ttatttaatg tccttttccaa    600 g                                                                  601
```

<210> SEQ ID NO 19
<211> LENGTH: 602
<212> TYPE: DNA
<213> ORGANISM: Homo sapiens
<220> FEATURE:
<221> NAME/KEY: misc_feature
<222> LOCATION: (333)..(333)
<223> OTHER INFORMATION: M=A/C

<400> SEQUENCE: 19

```
agctgaacat cttacaagac ttaaccaaac gaccagtaca aatgatgccc tagtagacac      60
acacacatac cttatatagc ttggtaaaca ggactcagtg gccagcttag ttaattcctc     120
attttaccac gaggaaaaaa tgctctctaa aaagcatttg ctagataaat acttgcttac    180
aagtcaaaat tagtgcatct taaccatttt gcacacaaat tcaaagatct ttttctccca     240
actctgacct gctgtcaatc aaaggggctg gggtaagtca aagttggatg aagttataag    300
aagccactat ttcccacttt accgcccagg camacacaaa catttgctga gtcattgata   360
atagtgcaag aattcagatc ccatggcatg aattatggat ggagtatcag cctttccctt    420
tgagtttcct ggcatttgat ggtccatatc acaataaaaa catacttctg agtctgtgaa    480
```

| tgtcttgggt gtcttctctc attctctctc tctctgggtg tgtgtgcatg tatgtgtctg | 540 |
| tctgtctctg tgtcactctc ttaataatag tcttttaact ccttcaaaaa gagttttgat | 600 |
| ca | 602 |

<210> SEQ ID NO 20
<211> LENGTH: 601
<212> TYPE: DNA
<213> ORGANISM: Homo sapiens
<220> FEATURE:
<221> NAME/KEY: misc_feature
<222> LOCATION: (301)..(301)
<223> OTHER INFORMATION: Y=C/T

<400> SEQUENCE: 20

| tgtttgctta agatgaaggt taaggagagg gcgtacttgc tgggagttca tggcggggaa | 60 |
| gataaacgcg gatgtttact atctaaatta cattcattac cttcatgcct tttcctcctt | 120 |
| ataattagtt ctctgacttt cttaggatat tttctaatgc aaaggtattt gtcagaaggc | 180 |
| agtcaaggcc gttgcatgtg gtttgtgttt tatgtttgcc tgttcctcgc ttgtccatag | 240 |
| agttggaggc cagaggggtg agaaaggaag ttttgttttg taagatgata tcccttcaac | 300 |
| ytactgtttg tttcacttat tttgttaatt tgactctttt ttttttttaaa gtagtttact | 360 |
| tagaatcctg tgttgcctct agtcagcttt tgttcatcta agatagtgtc agatgaggat | 420 |
| gctgctaggt aggaatgagc ctggtggtct cttacactgt cctcgacagg ttagaatctc | 480 |
| aaattcatca ccgtttagca accaggagta tttacagccc cttgcttcat cagggctaaa | 540 |
| tgtgaagcat ccccttggtg atacttaagg tgatatttaa gtgagtggga atgaaaaaca | 600 |
| g | 601 |

<210> SEQ ID NO 21
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: R=A/G

<400> SEQUENCE: 21

| aagatagtgt cagatgagga tgctgctagg taggaatgag cctggtggtc tcttacactg | 60 |
| tcctcgacag gttagaatct caaattcatc accgtttagc aaccaggagt atttacagcc | 120 |
| ccttgcttca tcagggctaa atgtgaagca tccccttggt gatacttaag gtgatattta | 180 |
| agtgagtggg aatgaaaaac rgaggaaata agcatttctt aagatgtgtg atttggggac | 240 |
| acccaatcaa taggtttagg aggaagagag aattgggact agctatctta tctcaaataa | 300 |
| tagaagtaag tgaaaggata aatattttga aaggactagt gtgaaatata catgaatgta | 360 |
| ttcctaggga ttctgctgcg gggtgggaaa ggggtgcaga t | 401 |

<210> SEQ ID NO 22
<211> LENGTH: 601
<212> TYPE: DNA
<213> ORGANISM: Homo sapiens
<220> FEATURE:
<221> NAME/KEY: misc_feature
<222> LOCATION: (301)..(301)
<223> OTHER INFORMATION: R=A/G

<400> SEQUENCE: 22

```
aggatgctgc taggtaggaa tgagcctggt ggtctcttac actgtcctcg acaggttaga        60
atctcaaatt catcaccgtt tagcaaccag gagtatttac agcccttgc ttcatcaggg        120 ctaaatgtga agcatcccct tggtgatact taaggtgata tttaagtgag tgggaatgaa       180
aaacagagga aataagcatt tcttaagatg tgtgatttgg ggacacccaa tcataggtt        240 taggaggaag agagaattgg gactagctat cttatctcaa ataatagaag taagtgaaag       300
rataaatatt ttgaaaggac tagtgtgaaa tatacatgaa tgtattccta gggattctgc      360
tgcggggtgg gaaaggggtg cagattaagc cagaccccat cattcatccc tggaaatgtg     420
ctcccacctc tagccaagag gcctgaggtc ccttctcaca acttcaaact ccctggaata      480
ccattaggtg gagcctaggg gactggctag gaggtgaagg tgtgagctcc atacctgcca    540
tttgcttgcc agtgacctca gggaagacac ctactctctc tgagcctgaa atttcccacc     600
t                                                                       601

<210> SEQ ID NO 23
<211> LENGTH: 501
<212> TYPE: DNA
<213> ORGANISM: Homo sapiens
<220> FEATURE:
<221> NAME/KEY: misc_feature
<222> LOCATION: (251)..(251)
<223> OTHER INFORMATION: R=A/G

<400> SEQUENCE: 23
aaaaaaaaag aatgtcatga cagtttgtat tgacagcctt tttctagcaa gaaacatacc       60
gttattttga acttgtgaat gatttatgaa ttgtgattct gtcttcagga tcctgttttt       120
ttctgttttg ttttttgttt tgtcatcaaa ttgccacagg ggggagtata agttcttgaa       180
agcagcaaga aatacagttt aagtaatttg gtaccaatta tcattattat tagaaacgtc      240
catatctgaa rcatctaaac agattagatt aataccctatg tgaaagtaga aatatttata    300
gtaaaaaatt gggcaccgtt taatatagga tttattaatt ttgtgatagt tgcaaaagct      360
gtgtctggaa aatgtcccca tgggtgaatg tgtgggcgtg cacatgcatg tgggtaatat     420
taatgctgta ggagaaggga gaaaatgtaa gtttctagtt tttgccatta aagtcatgac     480
gtgaaagaga gagggagaga g                                                 501

<210> SEQ ID NO 24
<211> LENGTH: 601
<212> TYPE: DNA
<213> ORGANISM: Homo sapiens
<220> FEATURE:
<221> NAME/KEY: misc_feature
<222> LOCATION: (301)..(301)
<223> OTHER INFORMATION: R=A/G

<400> SEQUENCE: 24
agacaaaggc tggaggtttt cacacctggt agtctcatgt agaaaggaag gctgatcagc        60
agggaggcag aggaagggtt gacagggtag gaccttggag ggaagcagtt aggcttggaa     120
gggacacaaa ggaaaggatg gcaaagaact gaccagagca actaaaagca caacatagta      180
gaaccgagga cacatctgag actagagacc acaaatgtat ggcagacact ataggaacaa   240
ctaaggcagg cactggcttg aagaaaggtc atgaggccaa aggccagaag tgtaacaagg   300
rgctgttggc ataaaacagt atgccatgga gagagaggaa gcaaaaccgt gtgtccagga  360 gaaaggaag gggcaagaga ccaaagtcac gatcaggtca aaacattgat gtgaagaata    420
aatgagcaag agaggccggg ggcggtggct cacgcctgta atcccagcac tttgggagac   480
```

```
cgaggtgggc agatcatgag gtcaggagat ggagaccatc ctggctaaca cggtgaaacc    540
ccgtctctac taaaagtaca aaaaacttag ccaggcgtgg tggcgggcgc ctgtagtccc    600
a                                                                    601
```

<210> SEQ ID NO 25
<211> LENGTH: 1982
<212> TYPE: DNA
<213> ORGANISM: Homo sapiens
<220> FEATURE:
<221> NAME/KEY: misc_feature
<222> LOCATION: (1102)..(1102)
<223> OTHER INFORMATION: M=A/C

<400> SEQUENCE: 25

```
caggaactca tcttaaatat ttaaaaataa gttttttttt ctaattgcaa ggaataagta     60
ctctttgtaa atgatatgga aagtatggaa tataataaag atgaaaaaga taactcctag    120
ataatcactt ttaatgtttt ggcaaaattc tttttaaaaa gtgctaaaga aaatgtggca    180
catatacatc atggaatact atgcatccat aaaaaagaat gagttcatgt cctttggagg    240
gacatagatg aagctgaaag ccatcattct tagcaaacta acccaggaac agaaaaccaa    300
acaccgcata ttctcactca taagtgggag ttgaacaatg agaacacatg gacacaggga    360
ggggaacatc acacatgggg gcctgttggg ggtgggggc caaggaaagg gaaaacatta    420
ggacaaatac ctaatgtatg cagagttaaa atctagatga cgggttgata ggtgcagcaa    480
accaccatgg cacgtgtata cctatgtaac aaatctgcac attctgcaca tgtatcccag    540
aacttaaagt aaaaaaaaaa aaagtgcttg aatatattta atttttaaac ttttttaattg    600 aaatataata gagatttaac aatatgtgcc aagttctctc atgcccccac ctccaaagta    660
accactaccc tgcctttatc actatttagt tttgcttcct cttcaatttc atatagatga    720
cattatgcag tgtgtatgct tttgtgcctg acttcttttca ctcaccataa tagtgctttt    780
cttttttata tataagagat ttattctgag ccaaatgatga gtgaccatgg cccatgacac    840
agccctcaag aggtcctgag aacttgtgcc caaggtggtc tggggggcagc ttggttttat    900 acatttaga gcagcatgag acatcaatca catccgttta agaaatacat tggtttggtc    960
cagatgtgga gcgggtggtg ggggaagggg aggcttccag gttataggtg aatttaaaca   1020
ttttctggtt gacaattggt tgagtttgtc tcaaaacgtg ggatagaggc tgggcgcagt   1080
ggctcacgcc tataatccca gmactttggg aggccgaggc gggcggatca cctgagctca   1140
gaagttcaag accagcctgg gcaacatggt gaaacccgt ctctattaaa aatacaaaaa    1200
atcagcctag tgtggtagtg catgcctgta atcccagcta ctcgggaggc tgaggcagga   1260
gaatcacttg aacccgggag gcagaggttg cagtgagtcg agatcacgcc actgcactcc   1320
ggcctgggcg acagagagag actttgtatc aaaaaaaaa aaaaaaaaaa aaggcctggg   1380
atagataaga agggaatgtt caggttaaga taaacattgt ggaaacccaa gttcttctga   1440
ggtcttatag tggctgcctg tagaggcaag aagtgacaaa tgtttcctat tcagatctca   1500
gttcatctct ttacgattgg gagagtctgc aagaaaaaga tctatctata ttaatagaga   1560
ttctttagag gtgcaaattt tccctcacaa agaacaactt tgcggggcca tttcaaaata   1620
tggcaaagaa acatgttttg gggaaatgca cttttttaatt gatgtatatt gttccattat   1680
ataaatattc tatactctat caattttct gtttacagaa ttcagatttt tgctttcagt    1740
ttttggatgg atgaaactgc tttgagaatt ttgtatgtct tttgctcact tctccttgaat   1800
```

```
atataccaaa gactaaaagt tattgtagtt atctaaatta tacatgttaa cttgctgaca    1860
aaaattgtgt tagaatttgt tgacctaatg taaaagtttt atattcttgc gatgcaaatt    1920
ctaattaatc aatggtgctc ctcatttctt actaactctt ctttgactct cttttaaaca    1980
tg                                                                   1982

<210> SEQ ID NO 26
<211> LENGTH: 978
<212> TYPE: DNA
<213> ORGANISM: Homo sapiens
<220> FEATURE:
<221> NAME/KEY: misc_feature
<222> LOCATION: (679)..(679)
<223> OTHER INFORMATION: R=A/G

<400> SEQUENCE: 26
aactatatca aactacaagg agcataagag tgaatatact cttacagata agaaaacaag     60
tttaaatata aagaagaaa taaacatatt gcaataaaaa gtaataaata ttgtggacag     120
gcaaagaaaa tccaatatgt ggagggtaga aattcttaaa gaagaaaaa aaatcctaaa    180 agctataagt caaaaaaaac tttactagaa taaaaaagta tttgaaagca caagttgaaa    240
gggtgtgcca tgtgcctaaa caaatcaact aacagcaaaa cacattctag taaaactgct    300
ggagtttaaa gaaagggaa aagctatttg aacatgaaga caaaagaac atgagcctta    360 taaataaaaa gaaaattagc tcatcgttag attttttta cagcaatact ttatgacaga    420
aaaaaatgga ataacttatt taagatactt aaggaaagaa aatgagagtc aagaaacttt    480
tatcctctaa aactgatttt caagaatgac ttgattcttg aaatcaaacc ttgaatgact    540
aggttcatcc ctgttgtcac aaatgacagg attcccttct tttttaatga atagtactcc    600
attgtgtata tacctcat cttctttacc catccatctg ttgatggaca cttaggttga    660
ttccataact tagctatcrt ggatagtgct gcaatgaaca ggaaggacac agacaaactg    720
ttaaaaacac acaagaactc agggcatatt tttcctgtga gcccttgctg aggaacctac    780
tagcaaacaa gctcaaacaa cacaaatgtc tgagagatac taacctaagg actgtagtga    840
gaattgaata tagctcacct ttagaactaa gactgaatga aggttaaaaa ggagaaagta    900
ctgtatacag tgtaaaaagt agaacatttc tgcctgttta tttgcatata tttattggca    960
tatatattta tttgcata                                                  978

<210> SEQ ID NO 27
<211> LENGTH: 701
<212> TYPE: DNA
<213> ORGANISM: Homo sapiens
<220> FEATURE:
<221> NAME/KEY: misc_feature
<222> LOCATION: (501)..(501)
<223> OTHER INFORMATION: Y=C/T

<400> SEQUENCE: 27
tcttttcaac atactgactt cttttcatt gagtgtatac ccagtaatgg gattgctata     60
tcatatagta attgtattct taattttta tggaactttc tgttttcat aatggccgta    120 ctaatttaca ttcctgccaa caatgcacag ggttttttt cctccacatc cttgctgaca    180
gttttgttat cttttgtttt tttgatagta gccatttaa caggtgtgaa gtgatagctc    240
attgtggttt tgatttgcat ttccctgatg gttagtaatg ttgaacattt tttcatatac    300
ttgttggcca tttgtgtgtc ttcttttgag aaacatctgt ctggtgacct gctcaattta    360
gattccactt ccaggagtat gaggatcttc tcctgggagg cagccctggc ttgtaagctt    420
```

```
tgttggagtg ctaggccaaa cccctactag attcaacagc tgctgtcagc ctggccttct    480
atatatctag tgactacctg ytggctgttt gagagctctc gtgttctcag aagcatcaga    540
taccttgttg tttctctgct tttctcacac atgtgctgac acggtgcaga tcttacggtg    600
gttgatgatt tggcaccccc tacctccgat atttgggggg tgaaagtgtg cattgccatc    660
taatttttgt agaaacattg cctgtgggat ttttgttttg c                       701
```

```
<210> SEQ ID NO 28
<211> LENGTH: 601
<212> TYPE: DNA
<213> ORGANISM: Homo sapiens
<220> FEATURE:
<221> NAME/KEY: misc_feature
<222> LOCATION: (301)..(301)
<223> OTHER INFORMATION: M=A/C

<400> SEQUENCE: 28
```

```
attggttatc atggcaacca aaacggaat tatacaaaac aagacttatg aaatagctcc     60
atttaaatga ggatttcatt tcataatttt cagatttaac agtaaggtaa tgaagttcag    120
aaacagacct agagcataaa attttaaaa aatgtaaaca ttttccacgt gcaaggcaca    180
tagactagtt tgtgatgtga agggttggaa actaacctat aacggccaga gaggtacaaa    240
tgccaaaagg accaagtgta atacaacagg gttaatggag actgaagtaa tctagagaga    300
mttgaattta aagtgtctat aaagttctgt gaagataaca aaaaaaatgg ctgtatagtc    360
aatgtggtgt gtatgcctgc aagtctgtga tacttgattc agtgtgaagt atgtttacat    420
aaaaattcta tggaataatc aatttattaa tgtatagaat aattaaagat atttagaaaa    480
ttattggtga attatcttat gattaataag aacttcctat ttatgctcaa gaaaactcag    540
aaatgtttag aaggataaat gaataaccaa gcccttata gaaaaatat acactttatt    600 t                                                                    601
```

```
<210> SEQ ID NO 29
<211> LENGTH: 406
<212> TYPE: DNA
<213> ORGANISM: Homo sapiens
<220> FEATURE:
<221> NAME/KEY: misc_feature
<222> LOCATION: (206)..(206)
<223> OTHER INFORMATION: Y=C/T

<400> SEQUENCE: 29
```

```
cctggaaatg tgctcccacc tctagccaag aggcctgagg tcccttctca caacttcaaa    60
ctccctggaa taccattagg tggagcctag gggactggct aggaggtgaa ggtgtgagct    120
ccatacctgc catttgcttg ccagtgacct cagggaagac acctactctc tctgagcctg    180
aaatttccca cctgttcaca gttaaygtgc agctcaagga gacaatattt atgaaagcac    240
tttcataaag gtattagagt tttaaaattg cccttctctt ccattcttca gtggctctca    300
aaactaagcc caactcagat tgactgtaaa agcctgtcac agtttgattt tataacagtg    360
tccagctctg catgggtttt agagtgttaa aactaggtga gagctc                  406
```

```
<210> SEQ ID NO 30
<211> LENGTH: 438
<212> TYPE: DNA
<213> ORGANISM: Homo sapiens
<220> FEATURE:
<221> NAME/KEY: misc_feature
<222> LOCATION: (201)..(201)
```

<223> OTHER INFORMATION: Y=C/T

<400> SEQUENCE: 30

```
tttttttctgt tttgttttg tttttgtcat caaattgcca caggggggag tataagttct      60
tgaaagcagc aagaaataca gtttaagtaa tttggtacca attatcatta ttattagaaa     120
cgtccatatc tgaaacatct aaacagatta gattaatacc tatgtgaaag tagaaatatt     180
tatagtaaaa aattgggcac ygtttaatat aggatttatt aattttgtga tagttgcaaa     240
agctgtgtct ggaaaatgtc cccatgggtg aatgtgtggg cgtgcacatg catgtgggta     300
atattaatgc tgtaggagaa gggagaaaat gtaagtttct agttttttgcc attaaagtca    360
tgacgtgaaa gagagaggga gagagagaaa gaaagtgaga aagtgctagt ctgtgtaaaa     420
tgaccatgaa agggcttg                                                    438
```

<210> SEQ ID NO 31
<211> LENGTH: 1001
<212> TYPE: DNA
<213> ORGANISM: Homo sapiens
<220> FEATURE:
<221> NAME/KEY: misc_feature
<222> LOCATION: (501)..(501)
<223> OTHER INFORMATION: R=A/G

<400> SEQUENCE: 31

```
tgtgtatagt atctcatata tatatatata tatatatttt ttcgggtttt cacgctcaaa      60
gtcctgccac catcgtaagt taccccaata tccacccaaa tcactatcca aactcacttc    120
taagctcctc ttgcctgtct cttctaagct agtcaggatt tgccatacac cctgccattt    180
catagaactt ctgcaatccc cttgggtcct tgatatggtt tggctctgtg tccccaccaa    240
atctcatgta agattgtaat ccccagtgtt ggaggtggag ctggtgggag gtgattggat    300
cataggggtg gtttctgaag gtttagcacc atcaccctgg tgctgtctca tgagagagtt    360
ctcatgaaat ctgcttgttt aaaagtgtcc cctttgttc ttttcttcct gctccagcca    420
tgtaggacgt gtctctttcc tctttgcttt ccgctgtgat tgcaagtttc ccgagacctc    480
cccagtcatg cttcctttac rgcctgcaga accatgaacc aattaaacct ctcttcttta    540
tagattatcc agtctcacgt agttctttat agcaatgtga gtacagacta atacagccct    600
acatttctgt cctctcctgc tctctcttgc tcatttattc ttttttttt gagacggagt    660
ctcgctctgt cgcccaggct ggagtgcagt tgggcgatct cggctcactg caagctccac    720
ctcctgggtt cacgccattc tcctgcctca gcctcccgag cagctgggac tacaggcgcc    780
cgccaccacg cctggctaag ttttttgtac ttttagtaga cggggtttt caccgtgtta    840
gccaggatgg tctccatctc ctgacctcat gatctgccca cctcggtctc ccaaagtgct    900
gggattacag gcgtgagcca ccgccccgg cctctcttgc tcatttattc ttcacatcaa    960
tgttttgacc tgatcgtgac tttggtctct tgccccttcc t                        1001
```

<210> SEQ ID NO 32
<211> LENGTH: 601
<212> TYPE: DNA
<213> ORGANISM: Homo sapiens
<220> FEATURE:
<221> NAME/KEY: misc_feature
<222> LOCATION: (301)..(301)
<223> OTHER INFORMATION: S=C/G

<400> SEQUENCE: 32

```
aatagtgctt ttctttttta tataagag atttattctg agccaaatat gagtgaccat       60
```

```
ggcccatgac acagccctca agaggtcctg agaacttgtg cccaaggtgg tctgggggca    120
gcttggtttt atacatttta gagcagcatg agacatcaat cacatccgtt taagaaatac    180
attggtttgg tccagatgtg gagcgggtgg tgggggaagg ggaggcttcc aggttatagg    240
tgaatttaaa cattttctgg ttgacaattg gttgagtttg tctcaagacg tgggatagag    300
sctgggcgca gtggctcacg cctataatcc cagcactttg ggaggccgag gcgggcggat    360
cacctgagct cagaagttca agaccagcct gggcaacatg gtgaaacccc gtctctatta    420
aaaatacaaa aaatcagcct agtgtggtag tgcatgcctg taatcccagc tactcgggag    480
gctgaggcag gagaatcact tgaacccggg aggcagaggt tgcagtgagt cgagatcacg    540
ccactgcact ccggcctggg cgacagagag agactttgta tcaaaaaaaa aaaaaaaaa    600 a                                                                      601
```

<210> SEQ ID NO 33
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 33
gctctcaaaa ctaagcccaa ctc                                              23

<210> SEQ ID NO 34
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 34
gagttgggct tagttttgag agc                                              23

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 35
gtaatataga agatgggtct a                                                21

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 36
gtaatataga tgatgggtct a                                                21

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 37
gaatatacaa cgaatatggg c                    21

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 38
gaatatacaa tgaatatggg c                    21

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 39
tggatgattc aaacaacttg g                    21

<210> SEQ ID NO 40
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 40
tggatgattc gaacaacttg g                    21

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
aaggggcaag agaccaaagt                      20

<210> SEQ ID NO 42
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 42
caccctgcca tttcatagaa c                    21

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
accagggtga tggtgctaaa                      20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
aatgaccatg aaagggcttg                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
tgcccccata tgtacagaaa                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
gggacatttt gcaagggtta                                              20

<210> SEQ ID NO 47
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 47
ttgctagaaa aaggctgtca a                                            21

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
cagcccaata ttccaccaag                                              20

<210> SEQ ID NO 49
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 49
gccaagttta ttttggcagg t                                            21

<210> SEQ ID NO 50
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 50
ttggttcttc ttgattgtgg ttt                                          23

```
<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
gcaaagcaac attggttcaa                                                   20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
ggtatgcttt gggaggctta                                                   20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
tctcagccga aacaagactg                                                   20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
tttagcggga acgcttctta                                                   20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
accgtgaaag ggctttgtaa                                                   20

<210> SEQ ID NO 56
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 56
tgctcagctt atttttgtca cc                                                22

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 57
ccctaactct ccccatcctc                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
atgtgcagct caaggagaca                                               20

<210> SEQ ID NO 59
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 59
ttgattttct ctgagctctc acc                                           23

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
taggaatgag cctggtggtc                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
ggtgtcccca aatcacacat                                               20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
tatgggcatc tggacagtga                                               20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
acgccctctc cttaaccttc                                               20

<210> SEQ ID NO 64
```

```
<210> SEQ ID NO 64
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 64
agcccctttg attgacagc                                                  19

<210> SEQ ID NO 65
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 65
gttaattcct cattttacca cga                                             23

<210> SEQ ID NO 66
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 66
agtccctcga agtctcaaaa a                                               21

<210> SEQ ID NO 67
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 67
gcacagaaac tttttctttc ctg                                             23

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
aagggtaggg atgtgcagtg                                                 20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
caggcatgaa gatggtggta                                                 20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
```

```
ggtgcaaaga tcggctttag                                               20

<210> SEQ ID NO 71
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 71
tcttcttggc tattttcaa caga                                           24

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
ggggttcacc taggagcatt                                               20

<210> SEQ ID NO 73
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 73
caagacaaac caaatccaat cc                                            22

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide4

<400> SEQUENCE: 74
tatcctcttc gcaccactcc                                               20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
gtggacagaa cagggcaaac                                               20

<210> SEQ ID NO 76
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 76
gcttacccgg ctgcagag                                                 18

<210> SEQ ID NO 77
<211> LENGTH: 18
<212> TYPE: DNA
```

<213> ORGANISM: Artificial Sequence
<220> FEATURE:
<223> OTHER INFORMATION: Synthetic oligonucleotide

<400> SEQUENCE: 77
acagccccga gacgacag                                            18

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
gcagcagctg gagaaagaaa                                          20

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 79
aaaaagaaac cgctcggact                                          20

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 80
ccaggcagtt ggctctaatc                                          20

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
tcagggtcgt gattctctcc                                          20

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
tggagatttt gggagtacgg                                          20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
tcaaacttcc tcccctcaaa                                          20

<210> SEQ ID NO 84
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 84
tgctcctaaa gccacacctt                                               20

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
ggaaaagatt cccacccaat                                               20

<210> SEQ ID NO 86
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 86
ccatttcatg ctttgaacga                                               20

<210> SEQ ID NO 87
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 87
ttgtgtgtgt gtgtgtgtgt gt                                            22

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
aatgccaaaa ggaccaagtg                                               20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
cagacttgca ggcatacaca                                               20

<210> SEQ ID NO 90
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 90
tggtttgtgg tgtggacagt                                                    20

<210> SEQ ID NO 91
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 91
ccacatgagg atagctgagg a                                                  21

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 92
gctttgttgg agtgctaggc                                                    20

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 93
ccaaatcatc aaccaccgta                                                    20

<210> SEQ ID NO 94
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 94
tttctgtaac ctggcttatt tca                                                23

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 95
tctgcacctc catgttcatt                                                    20

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 96
tttgtaggga tttggcttca                                                    20

```
<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 97
attgagtggg tcagggacaa                                                    20

<210> SEQ ID NO 98
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 98 ccctttctt taaactccag ca                                                  22

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
tggacaggca aagaaaatcc                                                    20

<210> SEQ ID NO 100
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 100
tgcaaataaa caggcagaaa tg                                                 22

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
gcccttgctg aggaacctac                                                    20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 102
acacatttct tgccccagac                                                    20

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 103 tcccctaca tctgcctaca                                                    20

<210> SEQ ID NO 104
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 104
agcctgtctt ctgaggcact                                                   20

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 105
gggggacaga gaaagactcc                                                   20

<210> SEQ ID NO 106
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 106
tgggtctaca tgtctattgc tttg                                              24

<210> SEQ ID NO 107
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 107
gggaatgccc atattcattg                                                   20

<210> SEQ ID NO 108
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 108
tggaaaccca agttcttctg a                                                 21

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 109
cccgcaaagt tgttctttgt                                                   20

<210> SEQ ID NO 110
<211> LENGTH: 19

```
<212> TYPE: DNA
<213> ORGANISM: Artificial Sequence
<220> FEATURE:
<223> OTHER INFORMATION: Synthetic oligonucleotide

<400> SEQUENCE: 110
ccatgacaca gccctcaag                                                   19

<210> SEQ ID NO 111
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 111
gcctctatcc cacgttttga                                                  20

<210> SEQ ID NO 112
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 112
tgtcctttgg agggacatag a                                                21

<210> SEQ ID NO 113
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 113
tatacacgtg ccatggtggt                                                  20

<210> SEQ ID NO 114
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 114
tgacttaatg aataagcctg ctg                                              23

<210> SEQ ID NO 115
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 115
gcaccatata aatgtgagat tgga                                             24

<210> SEQ ID NO 116
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 116
```

```
aaaagaagct gaatttgctt taaaat                                          26

<210> SEQ ID NO 117
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 117
agcaggatac tgacaggcaa a                                               21

<210> SEQ ID NO 118
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 118
tcatttaaaa ataaatccct ctgga                                           25

<210> SEQ ID NO 119
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 119
tgttttccat ttttcaatcc aa                                              22

<210> SEQ ID NO 120
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 120
ccagggtccc attcctagtt                                                 20

<210> SEQ ID NO 121
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 121
gaggcttgtg gagcattagc                                                 20

<210> SEQ ID NO 122
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 122
agcatgggtt tccatagcag                                                 20

<210> SEQ ID NO 123
<211> LENGTH: 20
<212> TYPE: DNA
<213> ORGANISM: Artificial Sequence
```

<220> FEATURE:
<223> OTHER INFORMATION: Synthetic oligonucleotide

<400> SEQUENCE: 123
tgtttgggat tgaggtcctt                                              20

<210> SEQ ID NO 124
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 124
tgtgcagttc aaacccatgt                                              20

<210> SEQ ID NO 125
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 125
tgtggtattg ggttgccatt                                              20

<210> SEQ ID NO 126
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 126
ttctccctac aggtcccaga                                              20

<210> SEQ ID NO 127
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 127
atgcactacc acactaggct ga                                           22

<210> SEQ ID NO 128
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 128
agcagcatga gacatcaatc ac                                           22

<210> SEQ ID NO 129
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 129
atgcactacc acactaggct ga                                           22

```
<210> SEQ ID NO 130
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 130
agcagcatga gacatcaatc ac                                              22

<210> SEQ ID NO 131
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 131
tgattcttga aatcaaacct tgaa                                            24

<210> SEQ ID NO 132
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 132
gctagtaggt tcctcagcaa gg                                              22

<210> SEQ ID NO 133
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 133
atggcaatgc acactttcac                                                 20

<210> SEQ ID NO 134
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 134
gctttgttgg agtgctaggc                                                 20

<210> SEQ ID NO 135
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 135
cttgcaggca tacacaccac                                                 20

<210> SEQ ID NO 136
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 136
aacggccaga gaggtacaaa                                               20

<210> SEQ ID NO 137
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 137
tgagagccac tgaagaatgg                                               20

<210> SEQ ID NO 138
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 138
taggtggagc ctaggggact                                               20

<210> SEQ ID NO 139
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 139
ggggacattt tccagacaca                                               20

<210> SEQ ID NO 140
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 140
tgtcatcaaa ttgccacagg                                               20

<210> SEQ ID NO 141
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 141
agcgagactc cgtctcaaaa                                               20

<210> SEQ ID NO 142
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 142
ctttgctttc cgctgtgatt                                               20
```

FIBROSIS SUSCEPTIBILITY GENE AND USES THEREOF

CROSS REFERENCE TO RELATED APPLICATIONS

This application is the national stage entry under 35 USC 371 for PCT/EP2010/052048, filed Feb. 18, 2010, which claims the benefit of the Feb. 19, 2009 priority date of European Application No. 09305159.7. The contents of both the foregoing applications are incorporated herein by reference.

FIELD OF THE INVENTION

The present invention relates generally to the fields of genetics and medicine. The present invention discloses in particular the identification of a human fibrosis susceptibility gene, which can be used for the diagnosis or prognosis of fibrosis or for the detection of predisposition to fibrosis, occurring in hepatic diseases, in cirrhosis, cutaneous keloid, obesity and any fibrotic disease. The invention more particularly discloses certain alleles of the CTGF gene on chromosome 6 related to susceptibility to fibrosis and representing novel targets for the screening of therapeutically active drugs. The present invention relates more specifically to particular mutations in the CTGF gene and expression products, as well as to diagnostic tools and kits based on these mutations. The invention can be also used for the prevention and/or treatment of fibrosis occurring in all the fibrotic human diseases.

BACKGROUND OF THE INVENTION

Fibrosis is an excessive growth of fibrous connective tissue in an organ, any part, or tissue thereof, for example in a liver, any part or tissue thereof, especially in response to an injury. Abnormal fibrosis occurs in chronic hepatic inflammations of various aetiologies such as in Hepatitis Virus and Schistosome infections. It was shown previously that certain subjects infected by Schistosomes are slow fibrosers whereas others are rapid fibrosers and that this depends in part on a major gene located on Chr 6q22-q23 (Dessein et al., 1999; Mohamed-Ali et al., 1999).

Schistosomiasis is caused by helminths that develop in the vascular system of their hosts and lay eggs that are for some of them carried over to the liver where they trigger inflammation in the periportal space. Since worms live for years in their human host, chronic liver inflammation associated with much tissue destruction is common in infected subjects. Tissue repair requires the deposit of extracellular matrix protein (ECMP) in the damaged tissues that are later on turned over and replaced by normal hepatocytes. In some patients ECMP accumulate in the periportal space forming fibrosis deposits that reduce blood flow causing varicose veins, ascites. After months or years of chronic or repeated injury, fibrosis becomes permanent and irreversible. Subjects die of the consequences of fibrosis.

In South countries, it is estimated that 5 to 10% of the 350 millions of infected subjects may develop severe hepatic fibrosis. There is no good marker allowing to predict and follow hepatic fibrosis progression in Schistosome infected subjects.

Diagnosis of hepatic fibrosis is mostly based on liver biopsy, elastometry (Boursier et al., 2008; Macias et al., 2008) and ultrasound analysis (Richter et al., 2001; Lambertucci et al., 2004; King et al., 2003).

Biopsies are obtained via percutanous, transjugular, radiographically-guided fine-needle or laparoscopic route, depending upon the clinical setting. Histopathological examination enables the clinician to grade the severity of necroinflammation and stage the extent of fibrosis. The Metavir scoring system attributes a score to the stages of fibrosis on a 1-4 scale as follows: F0=no fibrosis, F1=portal fibrosis without septa, F2=portal fibrosis and few septae, F3=numerous septae without cirrhosis, F4=cirrhosis (Bedossa et al., 1996). Liver biopsy is an invasive and costly procedure, and samples only a small portion of the liver. Thus it cannot afford a global assessment of hepatic fibrosis, and is subject to sampling variation and inter- and intra-observer error. In addition, liver biopsy is associated with significant morbidity of 3% and a mortality rate of 0.03% (Garcia-Tsao et al., 1993). Potential complications include local hematoma, infection and pain related to the biopsy.

Noninvasive tests (i.e., serologic markers, elastometry, ultrasound analysis) are also used but are not yet ready for routine clinical use.

Panels of blood markers have been tested mostly in patients with chronic hepatitis C or cirrhosis due to viral hepatitis C. These studies revealed that serum markers can rule on or rule out fibrosis in approximately 35% of patients (Sebastiani et al., 2006). However, when looking at patients individually, these markers could not reliably differentiate between the various stages of fibrosis. A more recent study incorporated three panels of serum markers to devise an algorithmic approach that improved diagnostic accuracy (Parkes et al., 2006). The three panels evaluated were the APRI (aspartate transaminase to platelet ratio index), the Forms' index (platelets, gammaglutamyltranspeptidase, cholesterol) and the Fibrotest (GGT, haptoglobin, bilirubin, apolipoprotein A, alpha-2-macroglobulin). An algorithm consisting of the APRI followed by the Fibrotest boosted the diagnostic accuracy of fibrosis to above 90%. This group estimated that use of this algorithm could obviate the need for up to 50% of liver biopsies. However, the individual stages of fibrosis are not distinguishable using this algorithm. The limitation of these serum markers is the possibility of false positives when there is highly active hepatic inflammation.

Fibroscan is another innovative approach to staging hepatic fibrosis, which is based on elastography, which provides rapid measurement of mean hepatic tissue stiffness (Ziol et al., 2005). A probe is employed to transmit a vibration of low frequency and amplitude into the liver. This vibration wave triggers an elastic shear wave, whose velocity through the liver is directly proportional to tissuestiffness measured in kilopascals (kPa). Sensitivity of the Fibroscan technique ranged from 79 to 95%, and specificity from 78 to 95%, compared to the liver biopsy. However, the limitations of this technique are associated with attenuation of elastic waves in fluid or adipose tissue, which would impair assessment of fibrosis in patients. In addition, Fibroscan is an extremely expensive instrument.

However, no efficient method exists to prognose the fibrosis progression and the treatment efficiency.

A large number of molecules have been tested for treatment of hepatic fibrosis. For example, corticosteroids have been used to suppress hepatic inflammation in autoimmune and alcoholic hepatitis (Czaja et al., 2003). Ursodeoxycholic acid has been proven to increase survival in PBC patients by binding bile acids, and thus also decreasing hepatic inflammation (Poupon et al., 1997). Neutralizing inflammatory cytokines with specific receptor antagonists (TNFalpha, IL-1 receptor antagonists) and prostaglandin E have been tested in murine models, but not yet in humans (Bruck et al., 1997).

Another attractive target in curtailing hepatic fibrosis is the downregulation of hepatic stellate cell activation. Interferon gamma is used in combination with ribavirin for therapy of hepatitis C infection. It is postulated that the antifibrotic effects of the interferons may be partially related to downregulation of stellate cell activation. This mechanism could explain the improvement in fibrosis described in patients with viral hepatitis C who do not have a virologic response to interferon alpha (Poynard et al., 1998).

Trials of antioxidants (nacetylcysteine, alpha-tocopherol) are currently underway in humans. Angiotensin II receptors are upregulated in stellate cell activation, thus angiotensin converting enzyme inhibitors and angiotensin receptor blockers have demonstrated antifibrotic activity in vitro and in animals. This has yet to be replicated in humans (Jonsson et al., 2001). Promoting matrix degradation through matrix metalloproteinases is an antifibrotic strategy shown to be beneficial in a murine model (Iimuro et al., 2003). Specific apoptosis of hepatic stellate cells is another interesting theoretical idea, but has not yet been investigated (Gressner et al., 1998). Treatments aimed at reversing the fibrosis are usually too toxic for long-term use (i.e., corticosteroids, penicillamine) or have no proven efficacy (i.e., colchicine).

In conclusion, efficient and well-tolerated antifibrotic drugs are currently lacking and current treatment of fibrosis is limited to withdrawal of the noxious agent.

It has been previously reported that fibrosis development is markedly influenced by a major locus on Chr 6q23 (Dessein et al., 1999). It has been also proposed that CTGF gene contributes to increasing fibrosis by synergizing with various pro-fibrogenic growth factors (Leask et al., 2006) including PGDF, VEGF and the master fibrogenic molecule TGF-β. More specifically CTGF acts as a TGF-β downstream modulator (Leask et al., 2006; Leask et al., 2003). It increases TGF-β binding to its receptor, interferes with the negative Smad-7 feedback loop on TGF-β. (Wahab et al., 2005); it inhibits receptor binding of the principal TGF-β antagonist BPM-7 (Abreu et al., 2002). An important consequence of CTGF action on TGF-β is the stimulation of the trans-differentiation of hepatic stellate cells and other parenchymal cells into ECMP producing myofibroblasts which is involved in progressive fibrotic process (Kalluri et al., 2003; Neilson et al., 2005). CTGF is also thought to increase ECMP networking trough its binding capacities to fibronectin domains on ECMP (Gressner et al., 2007; Yoshida et al., 2007). CTGF is produced by a variety of cells including hepatocytes (Kobayashi et al., 2005; Gressner et al., 2007), hepatic stellate cells, myofibroblasts and endothelial cells (Gressnet et al., 2008). An overexpression of CTGF transcripts have been reported in different tissues including liver (Rachfal et al., 2003) affected by fibrosis of different aetiological origin. Experimental work in rats has shown that inhibiting CTGF by siRNAs prevents or reduces tissue fibrosis (Li et al., 2006; George et al., 2007).

However, the genetic factors that control the human fibrosis susceptibility were not identified as well as their effect on fibrosis progression.

SUMMARY OF THE INVENTION

The purpose of the present invention is to provide a new genetic approach for fibrosis prognosis and treatment. The present invention now discloses the identification of a human fibrosis susceptibility gene locus, the CTGF gene locus (CCN2), which can be used for detecting predisposition to, diagnosis and prognosis of fibrosis, especially of hepatic fibrosis, as well as for the screening of therapeutically active drugs. The invention resides, in particular, in a method which comprises detecting in a sample from the subject the presence of an alteration in the CTGF gene locus (CCN2), the presence of said alteration being indicative of the presence or predisposition to fibrosis.

A particular object of this invention resides in an in vitro method of detecting predisposition to or diagnosis and/or prognosis of fibrosis occurring in a subject, the method comprising detecting the presence of an alteration in the CTGF gene or polypeptide in a sample from the subject, the presence of said alteration being indicative of the presence of fibrosis or the predisposition to fibrosis. A particular object of this invention resides in a method for assessment (prediction) of the progression of fibrosis.

In a preferred embodiment, said alteration is located within 20 kb, upstream the start codon of the CTGF gene and 20 kb, downstream the 3'UTR of the CTGF gene.

Preferably, the alteration lies in the surrounding sequences of 15.3 kb region, upstream the starting codon of the CTGF gene and 14.1 kb region, downstream the untranslated region (3'UTR).

In another preferred embodiment, said alteration is a mutation, an insertion or a deletion of one or more bases. In a more preferred embodiment, said alteration is one or several single nucleotide polymorphism(s) SNP(s) or a haplotype of SNPs associated with fibrosis. Preferably, said single nucleotide polymorphisms are SNPs flanking CTGF gene, which are allelic variants lying close to the CTGF gene.

The method of the invention allows for detection and prognosis of fibrosis which occurs in a human fibrotic disease selected from hepatic diseases fibrosis, cirrhosis, cutaneous keloid, hypertrophic scars and obesity. Especially, the hepatic fibrosis may be caused by hepatic A virus, hepatic B virus, hepatic C virus (HCV), *Schistosoma japonicum* (*S. japonicum*) or *Schistosoma mansoni* (*S. mansoni*) infection.

In a particular embodiment, the method comprises detecting the presence of SNP rs9402373 and/or rs6918698 in the CTGF gene locus in a biological sample of a subject infected with HCV, wherein the presence of an allele C at position rs9402373 and/or allele G at position rs6918698 is indicative of a risk of developing a hepatic fibrosis or of the development of a hepatic fibrosis, or of a poor prognostic of hepatic fibrosis in the subject.

Preferably, the alteration in the CTGF gene locus is determined by performing a selective hybridization assay, a sequencing assay, a microsequencing assay, and/or an allele-specific amplification assay.

In another aspect of the invention, said alteration in the CTGF gene is determined by restriction enzyme digestion, the detection of at least one said SNP being an indication of fibrosis.

This invention also relates to a method for selecting a therapeutic compound for a subject that has or is predisposed to develop fibrosis, said method comprising contacting a test compound with a CTGF polypeptide or gene or a fragment thereof and determining the ability of said test compound to enhance or reduce biological activity or function of a pathway related to the CTGF gene.

LEGEND TO THE FIGURES

FIG. 1: Correlation bins in the CTGF (=CCN2) gene locus in fishermen.

Thirty three markers were genotyped on 70 unrelated subjects as described in Materials and Methods. Correlations (r2 values) between SNPs were determined using Haploview software. The darkest colors indicate the strongest correlations. Correlation bins (r2>0.05) were as follows SNPs rs9321314, rs6940184, rs12523697, rs9493149 and rs12529636 were in bin 1; SNPs rs12527705 and rs12526196 in bin 2; SNPs rs9399005, rs6918698, and deletion/insertion (D/I) rs3037970 in bin 3; SNP rs2151532 and SNP rs1931002 in bin 4; SNPs rs9493150, rs928501, rs11966728, rs12198610 and a new insertion/deletion (132319925-/GAAA) were in bin 5; SNPs rs7747601, rs7768619 and rs9402373 in bin 6; SNPs rs12527379 and rs2095252 in bin 7.

Sequencing CCN2 (3.2 kb) and 15.3 kb upstream the starting codon and 14.1 kb in the 3'UTR region was done on 8 cases and 2 controls. It revealed 61 SNPs among whose 50 had been described before.

Since the inventors were looking for a gene with major effects they focused the study on 53 SNPs with a MAF>20%. 33 SNPs with a MAF>20% were genotyped on 70 fishermen. Correlations (r2 values) between SNPs were determined using Haploview software. Bottom figure shows $r^2$ values× 100. The darkest colors indicate the strongest correlations. Above this representation, a physical map with the relative position of each marker is also provided. These markers are grouped in seven correlation (r2=0.5) bins (I to VII).

SNPs rs9321314, rs6940184, rs12523697, rs9493149 and rs12529636 were in bin 1; SNPs rs12527705 and rs12526196 in bin 2; SNPs rs9399005, rs6918698 and D/I rs3037970 in bin 3; SNP rs2151532 and SNP rs1931002 in bin 4; SNPs rs9493150, rs928501, rs11966728, rs12198610 and a new insertion/deletion (132319925-/GAAA) were in bin 5; SNPs rs7747601, rs7768619 and rs9402373 in bin 6; SNPs rs12527379 and rs2095252 in bin 7.

Twenty two SNPs were further genotyped in the whole fisherman sample (201 controls and 99 cases). The results of the univariate analysis are shown on the top of FIG. 1 and in Tables 1 and 4. SNPs associated with hepatic fibrosis were SNP rs12527705 (p=0.02, OR=2.3) and SNP rs12526196 (p=0.02, or =2.2) in bin II, SNP rs9399005 (p=0.02, OR=2.2), SNP rs6918698 (p=0.02, OR=2) and D/I rs3037970 (p=0.003, OR=2.6) in bin III, SNP rs1931002 (p=0.004, OR=2.3) and rs2151532 (p=0.02, OR=1.98) in bin IV and SNP rs9402373 (p=0.015, OR=2) in bin VI. The analysis was adjusted on gender (p<0.001) exposure (fishing years: p<0.001, born on boat: p<0.01) and number of treatments (p<0.01).

In the present analysis, D/I rs3037970 excluded rs6918698 in a multivariate analysis testing simultaneously both SNPs. Likewise SNP rs1931002 excluded SNP rs2151532; SNP rs1256196 excluded SNP rs12527705 and SNP rs9399005. This indicated that SNPs or deletions rs12526196, rs30337970, rs1931002, rs9402373 had the strongest association with hepatic fibrosis (HF). When all four SNPs were tested in the same regression model (lower part Table 4), SNPs rs12526196 (p=0.007, OR=3), rs9402373 (p=0.002, OR=2.8) and rs1931002 (p=0.002, OR=2.8) showed independent associated with HF. An haplotype 1002C, 6196T, present in 53.9% controls and 67.5 cases was associated with HF (p<0.005). The inventors also tested a phenotype that associated advanced HF with evidence of portal hypertension. They found (154 controls and 151 cases) rs9402373 (p=0.005, OR=2.6) and rs3037970 (p=0.05, OR=2) were associated with that phenotype, SNP rs1256196 showed a trend for an association with this more severe disease phenotype (p=0.12). Gender (p=0.001) entered the model as covariate. This suggested that both rs9402373 and rs3037970 could have a more important contribution to severe disease.

Figure 2:
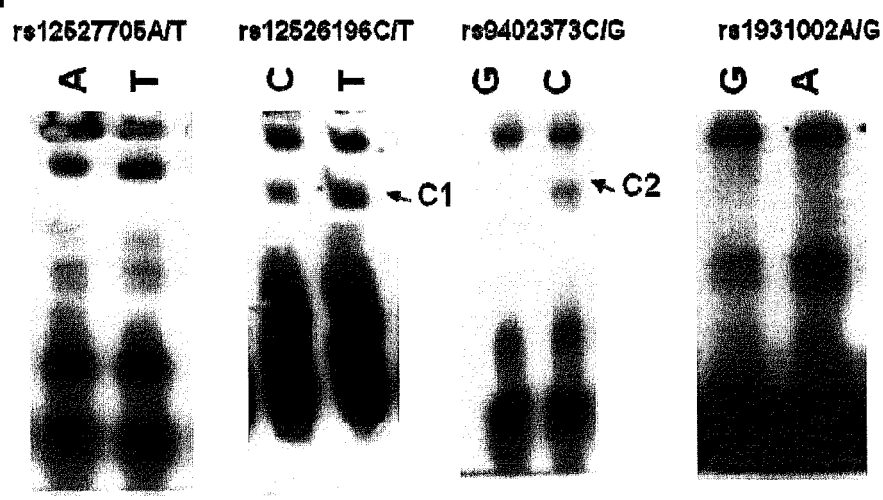
Figure 2:
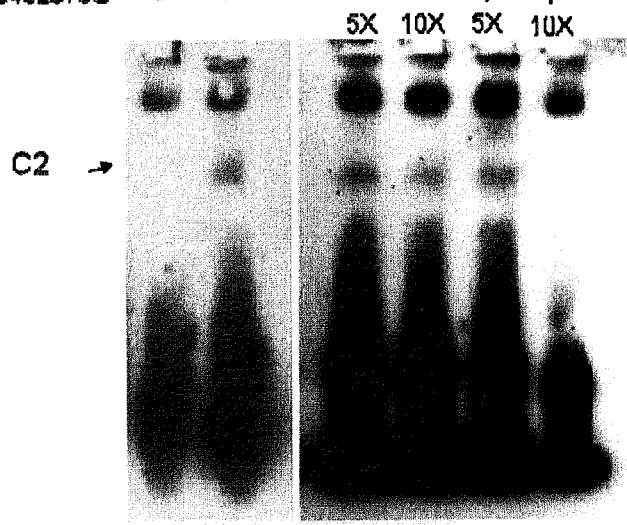

FIG. 2A: Electrophoretic mobility shift assay reveals allele specific binding of nuclear factors with SNPs rs12526196 and rs9402373.

EMSA were performed according to Materials and Methods using nuclear extracts of a stimulated human hepatocyte cell line (HEPG2). The 12526196T allele bound nuclear factors (complex 1) with a higher affinity than the C allele. SNP rs9402373C allele bound nuclear factors (complex 2) that were not bound by the G allele. No allele specific binding was observed with SNP rs12527705 and SNP rs1931002.

FIG. 2B: Competitive electrophoretic mobility shift assay for rs9402373 polymorphism. Competitive reactions were done with 100 or 200 fmol of unbiotinylated rs9402373G and C probe. Competitive reactions performed with unbiotinylated rs9402373C probe at concentration (200 fmol) but not with the unbiotinylated rs9402373G has competed the binding of the biotinylated rs9402373C probe.

Figure 3:
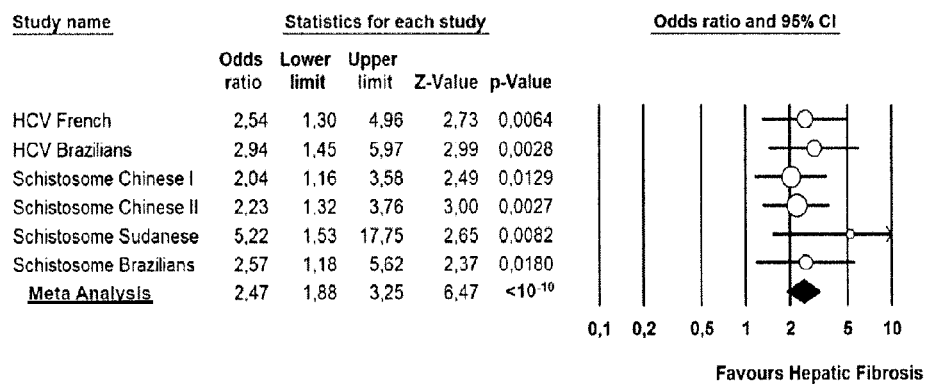

FIG. 3 shows the meta analysis of the association of SNP rs9402373 with hepatic fibrosis in HCV or Schistosome infected subjects.

DETAILED DESCRIPTION OF THE INVENTION

This invention identifies the most critical steps in fibrosis development and provides valuable genetic markers to predict disease progression in fibrosis, especially in hepatic fibrosis.

Early detection of fibrosis and regular monitoring of fibrosis, would allow for initiation of anti-fibrotic therapies capable of halting and even reversing this process. This would in turn prevent progression to human fibrosis disease, for example hepatic fibrosis or hepatic cirrhosis, and the morbidity and mortality this condition entails. The development of these various early fibrosis detection techniques bodes well for the future care of patients with liver disease.

The inventors have now identified the major gene associated with human fibrosis. They have shown that fibrosis in two Chinese, one Sudanese and one Brazilian cohort infected with *Schistosoma japonicum* and with *Schistosoma mansoni* respectively is markedly dependent on allelic variants lying in the CTGF gene. Two of these variants affect nuclear factor binding.

Various nucleic acid samples from individuals with fibrosis were submitted to a particular analysis process. Four populations with hepatic fibrosis were examined, inter alia a population of fishermen of the Dong Ting lake in central China infected with *Schistosoma japonicum*, a population of farmers living in Hunan province also infected with *Schistosoma japonicum*.

Two additional populations infected with *Schistosoma mansoni* were also included (a Sudanese and a Brazilian population). This analysis process led to the identification of particular single nucleotide polymorphism(s) SNP(s) in said populations that are overrepresented in subjects having hepatic fibrosis.

The inventors first examined fibrosis in Fishermen of the Dong Ting lake in central China near Yueyang city. Analysis of the various factors that influence the development of fibrosis in the fishermen population has shown that gender, exposure to infected waters and anti-schistosome treatments with Praziquantel were significantly associated with the risk of fibrosis. The testing of several covariates has shown that the "the number of years fishing" and "being born on a fishing boat" were the best covariates to measure exposure. The "treatment" covariate is the number of Praziquantel treatments over the last twenty years.

Using these covariates, the inventors tested on a population sample (N=300) whether SNPs (three per gene) in 12 candidate genes (two genes in the 6q23 region (IFNGR1, CTGF) and ten genes out of this region) were associated with the risk of fibrosis. One SNP rs9399005 near the CTGF gene yield a suggestive association (p=0.02) with fibrosis.

Then, the inventors sequenced the 3.2 kb of the CTGF gene and 15.3 kb upstream the starting codon and 14.1 kb in the 3'UTR region in 8 cases and 2 controls (fisherman population). 61 SNPs were recorded, among whose 50 had been described before. Fifty three SNPs (53 SNPs) had a MAF>20%. Since the inventors were looking for a gene with major effects, they selected SNPs with a MAF>20%. 33 out of 53 SNPs were genotyped on 70 fishermen.

They found seven correlation bins (r2=0.5), using data from the Hap Map project, that included 5, 2, 3, 2, 5, 3, 2 SNPs in bins I to VII respectively (FIG. 1). Finally, 22 SNPs or genetic variations were genotyped for further analysis. These 22 were added to the three SNPs tested in the early steps.

On these 25 SNPs or genetic variations (22+3) of the CTGF gene locus, 8 genetic variations were identified as being correlated to hepatic fibrosis in human subjects (rs12527705, rs12526196, rs9399005, rs6918698, rs3037970, 1931002, rs2151532 and rs9402373). Thus, a particular object of this invention resides in a method of detecting predisposition to and/or prognosis of fibrosis, the method comprising detecting the presence of one or several SNPs or alteration selected in the group consisting of rs12527705, rs12526196, rs9399005, rs6918698, rs3037970, 1931002, rs2151532 and rs9402373.

Among these SNPs, C allele of rs9402373 or T allele of rs12526196 specifically binds nuclear factors SRY, Lyf-1, CdxA, CP2, Ik-2, or Nkx-2.

SNPs rs6918698 and rs9402373 were shown to be associated with hepatis fibrosis in HCV infected subjects. In particular, allele C of rs9402373 was shown to be deleterious, i.e. it is strongly correlated with severe hepatic fibrosis.

Although the experimental data gathered by the inventors did not allow to confirm association of certain alleles, depending on the tested population, the present invention is not limited to the particular SNPs that were found significantly correlated with fibrosis in all tested populations. Indeed, several reasons could account for the failure in confirming significant correlation in some populations, including an insufficient cohort, the incomplete assessment of confounding variables, a lower frequency of the SNPs in said populations, etc.

DEFINITIONS

Within the context of this invention, "fibrosis" designates all types of human fibrosis occurring in all the fibrotic human diseases, for example in hepatic diseases, cirrhosis, cutaneous keloid, hypertrophic scars, sclerodermia, obesity and any fibrotic disease.

Within the context of this invention, "hepatic fibrosis" or "HF" designates all types of fibrosis occurring in a liver, tissue thereof or any part of tissue thereof. Hepatic fibrosis occurs especially in response to an injury. Hepatic fibrosis can be the common response to chronic liver injury, ultimately leading to cirrhosis and its complications, portal hypertension, liver failure, and hepatocellular carcinoma. Hepatic fibrosis is overly exuberant wound healing in which excessive connective tissue builds up in the liver. The extracellular matrix is either overproduced, degraded deficiently, or both. The trigger is chronic injury, especially if there is an inflammatory component. Various types of chronic liver injury can cause fibrosis, such as chemical fibrosis ($CCl_4$), bacterial (i.e., brucellosis), parasitic (i.e., bilharziosis/schistosomiasis caused by *Schistosoma* species; or echinococcosis infections) or viral (i.e., hepatitis caused by hepatic A virus (HAV), hepatic B virus (HBC) or hepatic C virus (HCV) infections).

Within the context of this invention, "cutaneous keloid" is an excessive growth of scar tissue on the skin. More particularly, keloids and hypertrophic scars (HSc) are dermal fibroproliferative disorders unique to humans that occur following trauma, inflammation, surgery, burns and sometimes spontaneously. These are characterized by excessive deposition of collagen in the dermis and the subcutaneous tissues. Contrary to the fine line scar characteristics of normal wound repair, the exuberant scarring of keloid and HSc results typically in disfigurement, contractures, pruritis and pain. Keloids occur in individuals with a familial disposition among the Blacks, Hispanics and Orientals. Unlike HSc, the keloid scars enlarge and extend beyond the margins of the original wound and rarely regress. These disorders represent aberrations in the fundamental processes of wound healing, which include cell migration and proliferation, inflammation, increased synthesis and secretion of cytokines and extra cellular matrix (ECM) proteins and remodelling of the newly synthesized matrix. Biologically, keloids are fibrotic tissue characterized by a collection of atypical fibroblasts with excessive deposition of extracellular matrix components, especially collagen, fibronectin, elastin, and proteoglycans. Generally, keloids contain relatively acellular centers and thick, abundant collagen bundles that form nodules in the deep dermal portion of the lesion. The release and activation of growth factors during the inflammatory phase of healing are pre-requisites for the scar processes, including angiogenesis, reepithelialization, recruitment and proliferation of fibroblasts and matrix deposition. Then, abnormal production of activity of the regulating cytokine including CTGF, could contribute to the development of keloids.

Within the context of this invention, "the CTGF gene locus" (Connection Tissue Growth Factor), also called CCN2 gene locus, designates all sequences or products in a cell or organism, including CTGF coding sequences, CTGF non-coding sequences (e.g., introns), CTGF regulatory sequences controlling transcription and/or translation (e.g., promoter, enhancer, terminator, etc.), all corresponding expression products, such as CTGF RNAs (e.g., mRNAs) and CTGF polypeptides (e.g., a pre-protein and a mature protein); as well as surrounding sequences of 20 kb region, preferably 15.3 kb region, upstream the starting codon of the CTGF gene and 20 kb region, preferably 14.1 kb region, downstream the untranslated region (3'UTR). For example, the CTGF locus comprises surrounding sequences comprising the 61 SNPs identified by sequencing (FIG. 1) and in particular 8 SNPs of Table 1. However in a particular embodiment most alterations are not in the promoter sequence.

Within the context of the present invention, the term "prognosis" includes the detection, monitoring, dosing, comparison, etc., at various stages, including early, pre-symptomatic stages, and late stages, in adults, children and pre-birth. Prognosis typically includes the assessment (prediction) of the progression of fibrosis and the characterization of a subject to define most appropriate treatment (pharmaco-genetics), etc. The present invention provides prognostic methods to determine the speed of the progression of fibrosis or an associated disorder resulting from a mutation or a polymorphism in the CTGF gene locus. Prognosis, which analyzes and predicts response to a treatment or drug, or side effects to a treatment or drug, aims at determining whether an individual should be treated with a particular treatment drug. For example, if the prognosis indicates a likelihood that an individual will respond positively to treatment with a particular drug, the drug may be administered to the individual. Conversely, if the prognostic indicates that an individual is likely to respond negatively to treatment with a particular drug, an alternative course of treatment may be prescribed. A negative response may be defined as either the absence of an efficacious response or the presence of toxic side effects. Clinical drug trials represent another application for the CTGF gene locus SNPs. One or more CTGF SNPs indicative of response to a drug or to side effects to a drug may be identified using the methods described above. Thereafter, potential participants in clinical trials of such an agent may be screened to identify those individuals most likely to respond favourably to the drug and exclude those likely to experience side effects. In that way, the effectiveness of drug treatment may be measured in individuals who respond positively to the drug, without lowering the measurement as a result of the inclusion of individuals who are unlikely to respond positively in the study and without risking undesirable safety problems.

Alterations

The alteration may be determined at the level of the CTGF DNA, RNA or polypeptide. Optionally, the detection is performed by sequencing all or part of the CTGF gene locus or by selective hybridization or amplification of all or part of the CTGF gene locus. More preferably a CTGF gene locus specific amplification is carried out before the alteration identification step. An alteration in the CTGF gene locus may be any form of mutation(s), deletion(s), rearrangement(s) and/or insertions in the coding and/or non-coding region of the locus, alone or in various combination(s). Mutations more specifically include point mutations. Deletions may encompass any region of two or more residues in a coding or non-coding portion of the gene locus, such as from two residues up to the entire gene or locus. Typical deletions affect smaller regions, such as domains (introns) or repeated sequences or fragments of less than about 50 consecutive base pairs, although larger deletions may occur as well. Insertions may encompass the addition of one or several residues in a coding or non-coding portion of the gene locus. Insertions may typically comprise an addition of between 1 and 50 base pairs in the gene locus. Rearrangement includes inversion of sequences. The CTGF gene locus alteration may result in the creation of stop codons, frameshift mutations, amino acid substitutions, particular RNA splicing or processing, product instability, truncated polypeptide production, etc. The alteration may result in the production of a CTGF polypeptide with altered function, stability, targeting or structure. The alteration may also cause a reduction in protein expression or, alternatively, an increase in said production.

In a preferred embodiment, said alteration is a mutation, an insertion or a deletion of one or more bases. In a particular embodiment of the method according to the present invention, the alteration in the CTGF gene locus is selected from a point mutation, a deletion and an insertion in the CTGF gene or corresponding expression product, more preferably a point mutation and a deletion. The alteration may be determined at the level of the CTGF DNA, RNA or polypeptide.

A particular object of this invention is a method of detecting predisposition to and/or prognosis of fibrosis, the method comprising detecting the presence of one or several alterations or SNPs selected in the group consisting of rs9402373, rs1931002, rs12526196, rs1257379, rs12527705, rs9399005, rs6918698, rs3037970, rs2151532, rs9321314, rs9321315, rs6910279, rs6940184, rs12523697, rs9493149, rs12529636, rs6917644, rs9493150, rs928501, rs11966728, rs7747601, rs12198610, 132319925 D/I, rs9483364, rs2095252, rs6926879, rs34118837, rs1931003, rs12191459, rs12206863, rs7768619, rs10872386 and rs2327184.

The 132319925 D/I (deletion/insertion) polymorphism is a new polymorphism that was never described before. To be able to identify this polymorphism the inventors gave as name the position according to the coordinate system and D/I to indicate that this polymorphism induces a deletion or an insertion. This polymorphism can be also written 132319925-/GAAA.

Preferably, said alteration(s) or SNP(s) associated with fibrosis is(are) selected from the group consisting of rs12527705, rs12526196, rs9399005, rs6918698, rs3037970, rs1931002, rs2151532 and rs9402373. More preferably, said rs9402373C and rs12526196T alleles preferentially bind nuclear factors.

These alterations/SNPs are reported in the following Table 1.

TABLE 1

Fibrosis-associated alterations in the CTGF gene locus

| Nucleotide position in genomic sequence of chromosome | Alteration/ SNP reference | Poly- morphism | Sequence reference |
|---|---|---|---|
| 132304944 | rs12527705 | A/T | SEQ ID NO: 1 |
| 132305169 | rs12526196 | C/T | SEQ ID NO: 2 |
| 132310657 | rs9399005 | C/T | SEQ ID NO: 3 |
| 132314950 | rs6918698 | C/G | SEQ ID NO: 4 |
| 132316891 | rs3037970 | -/TAAAA (D/I) | SEQ ID NO: 5 |
| 132320175 | rs1931002 | A/G | SEQ ID NO: 6 |
| 132316423 | rs2151532 | C/T | SEQ ID NO: 7 |
| 132319124 | rs9402373 | C/G | SEQ ID NO: 8 |
| 132321533 | rs12527379 | A/G | SEQ ID NO: 9 |
| 132294634 | rs9321314 | A/G | SEQ ID NO: 10 |
| 132294969 | rs9321315 | A/T | SEQ ID NO: 11 |
| 132295757 | rs6910279 | A/G | SEQ ID NO: 12 |
| 132299137 | rs6940184 | G/T | SEQ ID NO: 13 |
| 132299717 | rs12523697 | C/T | SEQ ID NO: 14 |
| 132300452 | rs9493149 | A/G | SEQ ID NO: 15 |
| 132301414 | rs12529636 | A/G | SEQ ID NO: 16 |
| 132307358 | rs6917644 | A/G | SEQ ID NO: 17 |
| 132315684 | rs9493150 | C/G | SEQ ID NO: 18 |
| 132317130 | rs928501 | A/C | SEQ ID NO: 19 |
| 132318298 | rs11966728 | C/T | SEQ ID NO: 20 |
| 132318597 | rs7747601 | A/G | SEQ ID NO: 21 |
| 132318713 | rs12198610 | A/G | SEQ ID NO: 22 |
| 132323491 | rs9483364 | A/G | SEQ ID NO: 23 |
| 132325281 | rs2095252 | A/G | SEQ ID NO: 24 |
| 132304054 | rs6926879 | A/C | SEQ ID NO: 25 |
| 132307157 | rs1931003 | A/G | SEQ ID NO: 26 |
| 132309432 | rs12191459 | C/T | SEQ ID NO: 27 |
| 132310735 | rs12206863 | A/C | SEQ ID NO: 28 |

TABLE 1-continued

Fibrosis-associated alterations in the CTGF gene locus

| Nucleotide position in genomic sequence of chromosome | Alteration/ SNP reference | Poly- morphism | Sequence reference |
|---|---|---|---|
| 132319026 | rs7768619 | C/T | SEQ ID NO: 29 |
| 132323557 | rs10872386 | C/T | SEQ ID NO: 30 |
| 132324717 | rs2327184 | A/G | SEQ ID NO: 31 |
| 132304021 | rs34118837 | C/G | SEQ ID NO: 32 |
| 132319925 | -(promoteur 5) | -/GAAA (D/I) | |

Alterations in the CTGF gene may be detected by determining the presence of an altered CTGF RNA expression. Altered RNA expression includes the presence of an altered RNA sequence, the presence of an altered RNA splicing or processing, the presence of an altered quantity of RNA, etc. These may be detected by various techniques known in the art, including by sequencing all or part of the CTGF RNA or by selective hybridisation or selective amplification of all or part of said RNA, for instance.

In a further variant, the method comprises detecting the presence of an altered CTGF polypeptide expression. Altered CTGF polypeptide expression includes the presence of an altered polypeptide sequence, the presence of an altered quantity of CTGF polypeptide, the presence of an altered tissue distribution, etc. These may be detected by various techniques known in the art, including by sequencing and/or binding to specific ligands (such as antibodies), for instance.

As indicated above, various techniques known in the art may be used to detect or quantify altered CTGF gene or RNA expression or sequence, including sequencing, hybridisation, amplification and/or binding to specific ligands (such as antibodies). Other suitable methods include allele-specific oligonucleotide (ASO), allele-specific amplification, Southern blot (for DNAs), Northern blot (for RNAs), single-stranded conformation analysis (SSCA), PFGE, fluorescent in situ hybridization (FISH), gel migration, clamped denaturing gel electrophoresis, heteroduplex analysis, RNase protection, chemical mismatch cleavage, ELISA, radio-immunoassays (RIA) and immuno-enzymatic assays (IEMA). Some of these approaches (e.g., SSCA and CGGE) are based on a change in electrophoretic mobility of the nucleic acids, as a result of the presence of an altered sequence. According to these techniques, the altered sequence is visualized by a shift in mobility on gels. The fragments may then be sequenced to confirm the alteration. Some others are based on specific hybridization between nucleic acids from the subject and a probe specific for wild-type or altered CTGF gene or RNA. The probe may be in suspension or immobilized on a substrate. The probe is typically labelled to facilitate detection of hybrids. Some of these approaches are particularly suited for assessing a polypeptide sequence or expression level, such as Northern blot, ELISA and RIA. These latter require the use of a ligand specific for the polypeptide, more preferably of a specific antibody.

In a preferred embodiment, the method comprises detecting the presence of an altered CTGF gene expression profile in a sample from the subject. As indicated above, this can be accomplished more preferably by sequencing, selective hybridisation and/or selective amplification of nucleic acids present in said sample.

Sequencing

Sequencing can be carried out using techniques well known in the art, using automatic sequencers. The sequencing may be performed on the complete CTGF gene locus or, more preferably, on specific domains thereof, typically those known or suspected to carry deleterious mutations or other alterations.

Amplification

Amplification is based on the formation of specific hybrids between complementary nucleic acid sequences that serve to initiate nucleic acid reproduction. Amplification may be performed according to various techniques known in the art, such as by polymerase chain reaction (PCR), ligase chain reaction (LCR), strand displacement amplification (SDA) and nucleic acid sequence based amplification (NASBA). These techniques can be performed using commercially available reagents and protocols. Preferred techniques use allele-specific PCR or PCR-SSCP. Amplification usually requires the use of specific nucleic acid primers, to initiate the reaction. Nucleic acid primers useful for amplifying sequences from the CTGF gene locus are able to specifically hybridize with a portion of the CTGF gene locus that flank a target region of said locus, said target region being altered in certain subjects having fibrosis or associated disorders. Examples of such target regions are provided in Table 2. Another particular object of this invention resides in a nucleic acid primer useful for amplifying sequences from the CTGF gene or locus including surrounding regions. Such primers are preferably complementary to, and hybridize specifically to nucleic acid sequences in the CTGF gene locus. Particular primers are able to specifically hybridize with a portion of the CTGF gene locus that flank a target region of said locus, said target region being altered in certain subjects having fibrosis or associated disorders. Primers that can be used to amplify CTGF target region comprising SNPs as identified in Table 2 may be designed based on their sequence or on the genomic sequence of CTGF.

The invention also relates to a nucleic acid primer, said primer being complementary to and hybridizing specifically to a portion of a CTGF gene locus coding sequence (e.g., gene or RNA) altered in certain subjects having fibrosis or associated disorders. In this regard, particular primers of this invention are specific for altered sequences in a CTGF gene locus or RNA. By using such primers, the detection of an amplification product indicates the presence of an alteration in the CTGF gene locus. In contrast, the absence of amplification product indicates that the specific alteration is not present in the sample. The invention also concerns the use of a nucleic acid primer or a pair of nucleic acid primers as described above in a method of detecting the presence of or predisposition to fibrosis or an associated disorder in a subject or in a method of assessing the response of a subject to a treatment of fibrosis or an associated disorder.

Selective Hybridization

Hybridization detection methods are based on the formation of specific hybrids between complementary nucleic acid sequences that serve to detect nucleic acid sequence alteration(s). A particular detection technique involves the use of a nucleic acid probe specific for wild-type or altered CTGF gene or RNA, followed by the detection of the presence of a hybrid. The probe may be in suspension or immobilized on a substrate or support (as in nucleic acid array or chips technologies). The probe is typically labeled to facilitate detection of hybrids. In this regard, a particular embodiment of this invention comprises contacting the sample from the subject with a nucleic acid probe specific for an altered CTGF gene locus, and assessing the formation of an hybrid. In a particular preferred embodiment, the method comprises contacting simultaneously the sample with a set of probes that are specific, respectively, for wild type CTGF gene locus and for various altered forms thereof. In this embodiment, it is possible to detect directly the presence of various forms of alterations in the CTGF gene locus in the sample. Also, various samples from various subjects may be treated in parallel.

Within the context of this invention, a probe refers to a polynucleotide sequence which is complementary to and capable of specific hybridization with a (target portion of a) CTGF gene or RNA, and which is suitable for detecting polynucleotide polymorphisms associated with CTGF alleles which predispose to or are associated with fibrosis. Probes are preferably perfectly complementary to the CTGF gene, RNA, or target portion thereof. Probes typically comprise single-stranded nucleic acids of between 8 to 1000 nucleotides in length, for instance of between 10 and 800, more preferably of between 15 and 700, typically of between 20 and 500. It should be understood that longer probes may be used as well. A preferred probe of this invention is a single stranded nucleic acid molecule of between 8 to 500 nucleotides in length, which can specifically hybridize to a region of a CTGF gene locus or RNA that carries an alteration.

The method of the invention employs a nucleic acid probe specific for an altered (e.g., a mutated) CTGF gene or RNA, i.e., a nucleic acid probe that specifically hybridizes to said altered CTGF gene or RNA and essentially does not hybridize to a CTGF gene or RNA lacking said alteration. Specificity indicates that hybridization to the target sequence generates a specific signal which can be distinguished from the signal generated through non-specific hybridization. Perfectly complementary sequences are preferred to design probes according to this invention. It should be understood, however, that certain mismatch may be tolerated, as long as the specific signal may be distinguished from non-specific hybridization.

Particular examples of such probes are nucleic acid sequences complementary to a target portion of the genomic region including the CTGF gene locus or RNA carrying a point mutation as listed in Table 1 above. More particularly, the probes can comprise a sequence selected from the group consisting of SEQ ID NO 1 to 8 or a fragment thereof comprising the SNP or a complementary sequence thereof.

The sequence of the probes can be derived from the sequences of the CTGF gene and RNA as provided in the present application. Nucleotide substitutions may be performed, as well as chemical modifications of the probe. Such chemical modifications may be accomplished to increase the stability of hybrids (e.g., intercalating groups) or to label the probe. Typical examples of labels include, without limitation, radioactivity, fluorescence, luminescence, enzymatic labelling, etc. The invention also concerns the use of a nucleic acid probe as described above in a method of detecting the presence of or predisposition to fibrosis or an associated disorder in a subject or in a method of assessing the response of a subject to a treatment of fibrosis or an associated disorder.

Specific Ligand Binding

As indicated above, alteration in the CTGF gene locus may also be detected by screening for alteration(s) in CTGF polypeptide sequence or expression levels. In this regard, contacting the sample with a ligand specific for a CTGF polypeptide and determining the formation of a complex is also described. Different types of ligands may be used, such as specific antibodies. In a specific embodiment, the sample is contacted with an antibody specific for a CTGF polypeptide and the formation of an immune complex is determined. Various methods for detecting an immune complex can be used, such as ELISA, radio-immunoassays (RIA) and immuno-enzymatic assays (IEMA). Within the context of this invention, an antibody designates a polyclonal antibody, a monoclonal antibody, as well as fragments or derivatives thereof having substantially the same antigen specificity. Fragments include Fab, Fab'2, CDR regions, etc. Derivatives include single-chain antibodies, humanized antibodies, polyfunctional antibodies, etc. An antibody specific for a CTGF polypeptide designates an antibody that selectively binds a CTGF polypeptide, i.e., an antibody raised against a CTGF polypeptide or an epitope-containing fragment thereof. Although non-specific binding towards other antigens may occur, binding to the target CTGF polypeptide occurs with a higher affinity and can be reliably discriminated from non-specific binding.

It is also disclosed a diagnostic kit comprising products and reagents for detecting in a sample from a subject the presence of an alteration in the CTGF gene locus or polypeptide, in the CTGF gene or polypeptide expression, and/or in CTGF activity. Said diagnostic kit comprises any primer, any pair of primers, any nucleic acid probe and/or any ligand, preferably antibody, described in the present invention. Said diagnostic kit can further comprise reagents and/or protocols for performing a hybridization, amplification or antigen-antibody immune reaction.

Linkage Disequilibirum

Once a first SNP has been identified in a genomic region of interest, more particularly in CTGF gene locus, other additional SNPs in linkage disequilibrium with this first SNP can be identified. Indeed, any SNP in linkage disequilibrium with a first SNP associated with fibrosis or an associated disorder will be associated with this trait. Therefore, once the association has been demonstrated between a given SNP and fibrosis, the discovery of additional SNPs associated with this trait can be of great interest in order to increase the density of SNPs in this particular region. Identification of additional SNPs in linkage disequilibrium with a given SNP involves: (a) amplifying a fragment from the genomic region comprising or surrounding a first SNP from a plurality of individuals; (b) identifying of second SNP in the genomic region harboring or surrounding said first SNP; (c) conducting a linkage disequilibrium analysis between said first SNP and second SNP; and (d) selecting said second SNP as being in linkage disequilibrium with said first marker. Sub-combinations comprising steps (b) and (c) are also contemplated. These SNPs in linkage disequilibrium can also be used in the methods according to the present invention, and more particularly in the diagnosic methods according to the present invention.

Causal Mutation

Mutations in the CTGF gene locus which are responsible for fibrosis may be identified by comparing the sequences of the CTGF gene locus from patients presenting fibrosis or an associated disorder and control individuals. Based on the identified association of SNPs of CTGF, the identified locus can be scanned for mutations. In a preferred embodiment, functional regions such as exons and splice sites, promoters and other regulatory regions of the CTGF gene locus are scanned for mutations. Preferably, patients presenting fibrosis carry the mutation shown to be associated with fibrosis and control individuals do not carry the mutation or allele associated with fibrosis. It might also be possible that patients presenting fibrosis carry the mutation shown to be associated with fibrosis with a higher frequency than control individuals. The method used to detect such mutations generally comprises the following steps: amplification of a region of the CTGF gene locus comprising a SNP or a group of SNPs associated with fibrosis from DNA samples of the CTGF gene locus from patients presenting fibrosis and control individuals; sequencing of the amplified region; comparison of DNA sequences of the CTGF gene from patients presenting fibrosis or an associated disorder and control individuals; determination of mutations specific to patients presenting fibrosis.

Drug Screening

New methods for the screening of drug candidates or leads are also described. These methods include binding assays and/or functional assays, and may be performed in vitro, in cell systems, in animals, etc. A particular object of this invention resides in a method of selecting biologically active compounds, said method comprising contacting in vitro a test compound with a CTGF gene or polypeptide according to the present invention and determining the ability of said test compound to bind said CTGF gene or polypeptide. Binding to said gene or polypeptide provides an indication as to the ability of the compound to modulate the activity of said target, and thus to affect a pathway leading to fibrosis in a subject. In a preferred embodiment, the method comprises contacting in vitro a test compound with a CTGF polypeptide or a fragment thereof according to the present invention and determining the ability of said test compound to bind said CTGF polypeptide or fragment. The fragment preferably comprises a binding site of the CTGF polypeptide. Preferably, said CTGF gene or polypeptide or a fragment thereof is an altered or mutated CTGF gene or polypeptide or a fragment thereof comprising the alteration or mutation. A particular object of this invention resides in a method of selecting compounds active on fibrosis, said method comprising contacting in vitro a test compound with a CTGF polypeptide according to the present invention or binding site-containing fragment thereof and determining the ability of said test compound to bind said CTGF polypeptide or fragment thereof. Preferably, said CTGF polypeptide or a fragment thereof is an altered or mutated CTGF polypeptide or a fragment thereof comprising the alteration or mutation. The method for the screening of drug candidates comprises contacting a recombinant host cell expressing a CTGF polypeptide according to the present invention with a test compound, and determining the ability of said test compound to bind said CTGF and to modulate the activity of CTGF polypeptide. Preferably, said CTGF polypeptide or a fragment thereof is an altered or mutated CTGF polypeptide or a fragment thereof comprising the alteration or mutation. The determination of binding may be performed by various techniques, such as by labelling of the test compound, by competition with a labelled reference ligand, etc. The method of selecting biologically active compounds also comprises contacting in vitro a test compound with a CTGF polypeptide and determining the ability of said test compound to modulate the activity of said CTGF polypeptide. Preferably, said CTGF polypeptide or a fragment thereof is an altered or mutated CTGF polypeptide or a fragment thereof comprising the alteration or mutation.

The method of selecting biologically active compounds for a subject that has or is predisposed to develop fibrosis, also comprises contacting in vitro a test compound with a CTGF gene according to the present invention and determining the ability of said test compound to modulate the expression of said CTGF gene. Preferably, said CTGF gene or a fragment thereof is an altered or mutated CTGF gene or a fragment thereof comprising the alteration or mutation.

The method of screening, selecting or identifying active compounds, particularly compounds active on fibrosis, also comprises contacting a test compound with a recombinant host cell comprising a reporter construct, said reporter construct comprising a reporter gene under the control of a CTGF gene promoter, and selecting the test compounds that modulate (e.g. activate or inhibit) expression of the reporter gene. Preferably, said CTGF gene promoter or a fragment thereof is an altered or mutated CTGF gene promoter or a fragment thereof comprising the alteration or mutation.

The above screening assays may be performed in any suitable device, such as plates, tubes, dishes, flasks, etc. Typically, the assay is performed in multi-wells plates. Several test compounds can be assayed in parallel. Furthermore, the test compound may be of various origin, nature and composition. It may be any organic or inorganic substance, such as a lipid, peptide, polypeptide, nucleic acid, small molecule, etc., in isolated or in mixture with other substances. The compounds may be all or part of a combinatorial library of products, for instance.

Pharmaceutical Compositions, Therapy

It is also described a pharmaceutical composition comprising (i) a CTGF polypeptide or a fragment thereof, a nucleic acid encoding a CTGF polypeptide or a fragment thereof, a vector or a recombinant host cell as described above and (ii) a pharmaceutically acceptable carrier or vehicle. The invention also relates to a method of treating or preventing fibrosis or an associated disorder in a subject, the method comprising administering to said subject a functional (e.g., wild-type) CTGF polypeptide or a nucleic acid encoding the CTGF gene locus. It is also described a method of treating or preventing fibrosis in a subject, the method comprising administering to said subject a compound that modulates, preferably that activates or mimics, expression or activity of a CTGF gene locus or protein according to the present invention. Said compound can be an agonist or an antagonist of CTGF, an antisense or a RNAi of CTGF, an antibody or a fragment or a derivative thereof specific to a CTGF polypeptide. In a particular embodiment of the method, the modulation is an inhibition. In another particular embodiment of the method, the modulation is an activation.

It is also disclosed the use of a functional CTGF polypeptide, a nucleic acid encoding the CTGF gene locus, or a compound that modulates expression or activity of a CTGF gene or protein according to the present invention, in the manufacture of a pharmaceutical composition for treating or preventing fibrosis in a subject. Said compound can be an agonist or an antagonist of CTGF, an antisense or an RNAi of CTGF, an antibody or a fragment or a derivative thereof specific to a CTGF polypeptide. In a particular embodiment of the method, the modulation is an inhibition. In another particular embodiment of the method, the modulation is an activation.

The present invention demonstrates the correlation between fibrosis and the CTGF gene locus. The invention thus provides a novel target of therapeutic intervention. Various approaches can be contemplated to restore or modulate the CTGF activity or function in a subject, particularly those carrying an altered CTGF gene locus. Supplying wild-type function to such subjects is expected to suppress phenotypic expression of fibrosis in a pathological cell or organism. The supply of such function can be accomplished through gene or protein therapy, or by administering compounds that modulate or mimic CTGF polypeptide activity (e.g., agonists as identified in the above screening assays).

The wild-type CTGF gene or a functional part thereof may be introduced into the cells of the subject in need thereof using a vector as described above. The vector may be a viral vector or a plasmid. The gene may also be introduced as naked DNA. The gene may be provided so as to integrate into the genome of the recipient host' cells, or to remain extrachromosomal. Integration may occur randomly or at precisely defined sites, such as through homologous recombination. In particular, a functional copy of the CTGF gene may be inserted in replacement of an altered version in a cell, through homologous recombination. Further techniques include gene gun, liposome-mediated transfection, cationic lipid-mediated transfection, etc. Gene therapy may be accomplished by direct gene injection, or by administering ex vivo prepared genetically modified cells expressing a functional CTGF polypeptide.

Other molecules with CTGF activity (e.g., peptides, drugs, CTGF agonists, or organic compounds) may also be used to restore functional CTGF activity in a subject or to suppress the deleterious phenotype in a cell. Restoration of functional CTGF gene locus function in a cell may be used to prevent the development of fibrosis or to reduce progression of said disease.

Further aspects and advantages of the present invention will be disclosed in the following experimental section, which should be regarded as illustrative and not limiting the scope of the present application.

Materials and Methods

Statistical Analysis

Multivariate logistic regression was used to analyse the relationship between the probability of an individual developing fibrosis and genetic variants including the main covariates known to affect disease progression in subjects infected with schistosomes. The statistical SPSS software (version 10.0) was used for this analysis. Age and gender were tested in the regression models and kept when they showed an association ($p<0.05$) with disease. Since the cohorts were matched for gender and age, these covariates had little effects on the association between genetic variants and disease. The number of Praziquantel treatments, infection with HBV and exposure to infection were included in the regression models when these covariates could be evaluated accurately as in the Chinese fishermen (exposure, number of treatments) or in the Chinese farmers (HBV infection, place of birth).

DNA Extraction

Aliquots of 5 to 15 ml of blood were collected on sodium citrate and kept at $-20°$ C. DNA was extracted using the standard salting out method (Sambrook et al., 1989). Some subjects refused bleeding. In this case, buccal cell samples were collected using foam-tipped applicators and applied to indicating FTA1 cards following the protocol described by Whatman (http://www.whatman.co.uk/). Place the indicating FTA1 card on a clean, dry, flat surface. Label the FTA1 card with a unique identifying name or number. Remove one foam-tipped applicator from the protective packaging. Holding the plastic handle of the applicator, place the foam tip in the mouth and rub one side of the foam tip on the inside of the cheek for 30 s. Repeat using the opposite side of the foam tip for the other cheek. Run the foam tip along the gum-line and fold of the cheek and under the tongue, soaking up as much saliva as possible. Remove the applicator from the mouth. Carefully lift the paper cover of the indicating FTA1 card and press the flat and circular foam applicator tip with the sample area. Without lifting the foam tip from the card. Squeeze the tip using a side to side motion (908 in each direction) three times to completely saturate the sample area. The sample area will turn white upon transfer of the sample. Position the FTA1 card for drying on a clean surface. Allow the card to dry at least 1 h at room temperature. Afterwards the punches are washed three times in 200 µl of FTA purification buffer and in TE buffer successfully.

DNA Amplification

All the DNA purified from FTA card were pre amplified before genotyping. Polymerase chain reactions (whole genome amplifications) were conducted in 50 µl reactions containing one punch of biological sample (FTA1-bound buccal cell DNA) or 100 ng of genomic DNA, 1.5 OD of 15-base totally degenerate random primer (Genetix, Paris, France), 200 mM dNTPs, 5 mM $MgCl_2$, 5 ml of 10×PCR buffer and 0.5 unit of high fidelity Taq DNA polymerase (BIOTAQ DNA Polymerase, Bioline London, England). Samples were amplified in a multiblock thermocycler as follows: a pre-denaturation step of 3 min at $94°$ C., 50 cycles consisting of 1 min at $94°$ C., 2 min at $37°$ C., 1 min of ramp ($37-55°$ C.), and 4 min at $55°$ C. Final extension step of 5 min at $72°$ C.

Sequencing

Purified PCR products were sequenced using ABI Prism BigDye Terminator cycle sequencing system (PE Applied Biosystems, Foster City, U.S.A.) on ABI Prism automatic sequencer. Sequencing reactions were performed on both strands Sequencing by GATC biotech (GATC, Marseille France). The sequencing primers are described in Table 2. Sequencing CCN2 (3.2 kb) and 15.3 kb upstream the starting codon and 14.1 kb in the 3'UTR region in eight cases and two controls revealed 61 SNPs (FIG. 1) among whose 50 had been described before.

Polymorphism Genotyping by PCR with Specific Taqman Probes

Allelic discrimination was assessed using TaqMan probe assays (Applied Biosystems, Lafayette USA). Each reaction contained 12.5 ng of genomic DNA, TaqMan Universal PCR Master Mix (Applied Biosystems, Lafayette USA), 900 nM of each primer and 200 nM of each fluorescently-labelled hybridisation probe in a total volume of 5 µl. RT-PCR was conducted in an ABI Prism Sequence Detection System 7900 (Applied Biosystems, Lafayette USA) using the following conditions: $50°$ C. for 2 min, $95°$ C. for 10 min and 40 cycles of amplification ($95°$ C. denaturation for 15 s, $60°$ C. annealing/extension for 1 min). The following SNPs or alterations were genotyped by this methodology: rs9321314, rs9321315, rs6910279, rs6940184, rs12523697, rs9493149 rs12529636, rs12527705, rs12526196, rs6917644, rs9399005, rs6918698, rs9493150, rs2151532, rs3037970, rs928501, rs11966728, rs7747601, rs12198610, rs9402373, 132319925 D/I, rs1931002, rs12527379, rs9483364, rs2095252.

Polymorphism Genotyping by PCR and Restriction Enzyme Digestion

Polymorphisms (rs6926879, rs34118837, rs1931003, 12191459, rs12206863, 7768619, rs10872386 and rs2327184) were genotyped by restriction enzyme analysis under standard conditions described by the enzyme manufacturers (Euromedex, Mundolsheim, France or New England Biolabs, Beverly, USA). Polymerase chain reaction (PCR) amplifications were carried out on a robocycler gradient 96 (Stratagene, La Jolla, U.S.A.) according to standard protocol. Each digestion was resolved on either agarose or acrylamide gels, stained with ethidium bromide and visualized by UV. Primers are described in Table 2.

Nuclear Extract Preparation

Nuclear extracts were prepared from human hepatocyte cell line (HEPG2) stimulated for one hour with dexamethasone (1 mM) since hepatocytes produce CTGF in hepatic fibrosis (HF) Kobayashi et al., 2005, Gressner et al., 2007) together with hepatic stelate cells, and endothelial cells and myo-fibroblasts (Gressner et al., 2008). The extracts were prepared with the nuclear and cytoplasmic extraction reagents from Pierce (NE-PER; Pierce, Rockford, Ill., USA).

Electrophoretic Mobility Shift Assay (EMSA)

Complementary single-stranded oligonucleotides were commercially synthetised to span approximately 10 bp on either side of the variant nucleotide, as follows:

```
rs9402373C
                                    (SEQ ID NO: 33)
GCTCTCAAAACTAAGCCCAACTC rs9402373G
                                    (SEQ ID NO: 34)
GAGTTGGGCTTAGTTTTGAGAGC rs12527705A
                                    (SEQ ID NO: 35)
GTAATATAGAAGATGGGTCTA rs12527705T
                                    (SEQ ID NO: 36)
GTAATATAGATGATGGGTCTA rs12526196C
                                    (SEQ ID NO: 37)
GAATATACAACGAATATGGGC rs12526196T
                                    (SEQ ID NO: 38)
GAATATACAATGAATATGGGC rs1931002A
                                    (SEQ ID NO: 39)
TGGATGATTCAAACAACTTGG rs1931002G
                                    (SEQ ID NO: 40)
TGGATGATTCGAACAACTTGG
```

Complementary strands were annealed by placing reactions (oligonucleotide sens and oligonucleotide antisens) in boiling water for 10 min and allowing to cool to room temperature. Binding reactions were set up with LightShift Chemiluminescent EMSA Kit (Pierce, Rockford, Ill., USA). Aliquots of 20 fmol of complementary DNA were incubated at room temperature for 20 min with 4 mg of nuclear extract in 10 mM Tris, 50 mM KCl, 1 mM DTT, 2.5% glycerol, 5 mM $MgCl_2$, 50 ng/µl poly d(I-C), 0.05% NP-40, pH 7.5. Then reactions were loaded onto an 8% non-denaturing polyacrylamide gel and run for 150 min at 110V. Free DNA and DNA/protein complexes were transferred to nylon N+ membrane by capillary action. Binding was detected according to manufacturer's instructions (Pierce, Rockford, Ill., USA).

TABLE 2

| Primers used to prepare templates for sequencing | | | |
|---|---|---|---|
| Primer sequences (forward and reverse) | | Position according to the coordinate system. | PCR product size |
| AAGGGGCAAGAGACCAAAGT | (SEQ ID NO: 41) | 132325212-132325194 | 831 bp |
| CACCCTGCCATTTCATAGAAC | (SEQ ID NO: 42) | 132324384-132324404 | |
| ACCAGGGTGATGGTGCTAAA | (SEQ ID NO: 43) | 132324557-132324538 | 783 bp |
| AATGACCATGAAAGGGCTTG | (SEQ ID NO: 44) | 132323775-132323794 | |
| TGCCCCCATATGTACAGAAA | (SEQ ID NO: 45) | 132323861-132323842 | 844 bp |
| GGGACATTTTGCAAGGGTTA | (SEQ ID NO: 46) | 132323018-132323037 | |
| TTGCTAGAAAAAGGCTGTCAA | (SEQ ID NO: 47) | 132323290-132323270 | 827 bp |
| CAGCCCAATATTCCACCAAG | (SEQ ID NO: 48) | 132322464-132322483 | |
| GCCAAGTTTATTTTGGCAGGT | (SEQ ID NO: 49) | 132322614-132322593 | 826 bp |
| TTGGTTCTTCTTGATTGTGGTTT | (SEQ ID NO: 50) | 132321788-132321810 | |
| GCAAAGCAACATTGGTTCAA | (SEQ ID NO: 51) | 132321921-132321912 | 844 bp |
| GGTATGCTTTGGGAGGCTTA | (SEQ ID NO: 52) | 132321088-132321107 | |
| TCTCAGCCGAAACAAGACTG | (SEQ ID NO: 53) | 132321195-132321176 | 756 bp |
| TTTAGCGGGAACGCTTCTTA | (SEQ ID NO: 54) | 132320440-132320459 | |
| ACCGTGAAAGGGCTTTGTAA | (SEQ ID NO: 55) | 132320556-132320537 | 808 bp |
| TGCTCAGCTTATTTTGTCACC | (SEQ ID NO: 56) | 132319749-132319770 | |
| CCCTAACTCTCCCCATCCTC | (SEQ ID NO: 57) | 132319847-132319828 | 823 bp |
| ATGTGCAGCTCAAGGAGACA | (SEQ ID NO: 58) | 132319044-132319025 | |
| TTGATTTTCTCTGAGCTCTCACC | (SEQ ID NO: 59) | 132319238-132319216 | 812 bp |
| TAGGAATGAGCCTGGTGGTC | (SEQ ID NO: 60) | 132318427-132318446 | |
| GGTGTCCCCAAATCACACAT | (SEQ ID NO: 61) | 132318639-132318620 | 838 bp |
| TATGGGCATCTGGACAGTGA | (SEQ ID NO: 62) | 132317802-132317821 | |
| ACGCCCTCTCCTTAACCTTC | (SEQ ID NO: 63) | 132318031-132318012 | 838 bp |
| AGCCCTTTGATTGACAGC | (SEQ ID NO: 64) | 132317194-132317212 | |
| GTTAATTCCTCATTTTACCACGA | (SEQ ID NO: 65) | 132317353-132317331 | 647 bp |
| AGTCCCTCGAAGTCTCAAAAA | (SEQ ID NO: 66) | 132316706-132316726 | |
| GCACAGAAACTTTTTCTTTCCTG | (SEQ ID NO: 67) | 132316835-132316813 | 625 bp |
| AAGGGTAGGGATGTGCAGTG | (SEQ ID NO: 68) | 132316211-132316230 | |

TABLE 2-continued

Primers used to prepare templates for sequencing

| Primer sequences (forward and reverse) | | Position according to the coordinate system. | PCR product size |
|---|---|---|---|
| CAGGCATGAAGATGGTGGTA | (SEQ ID NO: 69) | 132316364-132316345 | 679 bp |
| GGTGCAAAGATCGGCTTTAG | (SEQ ID NO: 70) | 132315687-132315706 | |
| TCTTCTTGGCTATTTTTCAACAGA | (SEQ ID NO: 71) | 132315803-132315780 | 739 bp |
| GGGGTTCACCTAGGAGCATT | (SEQ ID NO: 72) | 132315065-132315084 | |
| CAAGACAAACCAAATCCAATCC | (SEQ ID NO: 73) | 132315178-132315157 | 706 bp |
| TATCCTCTTCGCACCACTCC | (SEQ ID NO: 74) | 132314474-132314493 | |
| GTGGACAGAACAGGGCAAAC | (SEQ ID NO: 75) | 132314570-132314551 | 637 bp |
| GCTTACCCGGCTGCAGAG | (SEQ ID NO: 76) | 132313934-132313951 | |
| ACAGCCCCGAGACGACAG | (SEQ ID NO: 77) | 132314127-132314110 | 635 bp |
| GCAGCAGCTGGAGAAAGAAA | (SEQ ID NO: 78) | 132313593-132313512 | |
| AAAAAGAAACCGCTCGGACT | (SEQ ID NO: 79) | 132313535-1323135016 | 602 bp |
| CCAGGCAGTTGGCTCTAATC | (SEQ ID NO: 80) | 132312934-132312953 | |
| TCAGGGTCGTGATTCTCTCC | (SEQ ID NO: 81) | 132313102-132313083 | 746 bp |
| TGGAGATTTTGGGAGTACGG | (SEQ ID NO: 82) | 132312357-132312376 | |
| TCAAACTTCCTCCCCTCAAA | (SEQ ID NO: 83) | 132312529-132312510 | 704 bp |
| TGCTCCTAAAGCCACACCTT | (SEQ ID NO: 84) | 132311826-132311845 | |
| GGAAAAGATTCCCACCCAAT | (SEQ ID NO: 85) | 132311978-1323119459 | 659 bp |
| CCATTTCATGCTTTGAACGA | (SEQ ID NO: 86) | 132311320-132311339 | |
| TTGTGTGTGTGTGTGTGTGT | (SEQ ID NO: 87) | 132311497-132311476 | 806 bp |
| AATGCCAAAAGGACCAAGTG | (SEQ ID NO: 88) | 132310673-132310692 | |
| CAGACTTGCAGGCATACACA | (SEQ ID NO: 89) | 132310821-132310802 | 844 bp |
| TGGTTTGTGGTGTGGACAGT | (SEQ ID NO: 90) | 132309978-132309997 | |
| CCACATGAGGATAGCTGAGGA | (SEQ ID NO: 91) | 132310141-132310121 | 794 bp |
| GCTTTGTTGGAGTGCTAGGC | (SEQ ID NO: 92) | 132309348-132309367 | |
| CCAAATCATCAACCACCGTA | (SEQ ID NO: 93) | 132309544-132309525 | 828 bp |
| TTTCTGTAACCTGGCTTATTTCA | (SEQ ID NO: 94) | 132308717-132308739 | |
| TCTGCACCTCCATGTTCATT | (SEQ ID NO: 95) | 132308929-132308910 | 845 bp |
| TTTGTAGGGATTTGGCTTCA | (SEQ ID NO: 96) | 132308085-132308104 | |
| ATTGAGTGGGTCAGGGACAA | (SEQ ID NO: 97) | 132308323-132308304 | 806 bp |
| CCCTTTTCTTTAAACTCCAGCA | (SEQ ID NO: 98) | 132307518-132307539 | |
| TGGACAGGCAAAGAAAATCC | (SEQ ID NO: 99) | 132307722-132307703 | 833 bp |
| TGCAAATAAACAGGCAGAAATG | (SEQ ID NO: 100) | 132306889-132306911 | |
| GCCCTTGCTGAGGAACCTAC | (SEQ ID NO: 101) | 132307075-132307056 | 846 bp |
| ACACATTTCTTGCCCCAGAC | (SEQ ID NO: 102) | 132306230-132306250 | |
| TCCCCCTACATCTGCCTACA | (SEQ ID NO: 103) | 132306391-132306072 | 839 bp |
| AGCCTGTCTTCTGAGGCACT | (SEQ ID NO: 104) | 132305563-132305572 | |
| GGGGGACAGAGAAAGACTCC | (SEQ ID NO: 105) | 132305749-132305730 | 803 bp |
| TGGGTCTACATGTCTATTGCTTTG | (SEQ ID NO: 106) | 132304957-132304970 | |
| GGGAATGCCCATATTCATTG | (SEQ ID NO: 107) | 132305185-132305166 | 814 bp |
| TGGAAACCCAAGTTCTTCTGA | (SEQ ID NO: 108) | 132304372-132304392 | |
| CCCGCAAAGTTGTTCTTTGT | (SEQ ID NO: 109) | 132304558-132304539 | 775 bp |
| CCATGACACAGCCCTCAAG | (SEQ ID NO: 110) | 132303384-132303402 | |
| GCCTCTATCCCACGTTTTGA | (SEQ ID NO: 111) | 132304022-132304003 | 843 bp |
| TGTCCTTTGGAGGGACATAGA | (SEQ ID NO: 112) | 132303180-132303200 | |
| TATACACGTGCCATGGTGGT | (SEQ ID NO: 113) | 132303452-132303433 | 792 bp |
| TGACTTAATGAATAAGCCTGCTG | (SEQ ID NO: 114) | 132302661-132302683 | |
| GCACCATATAAATGTGAGATTGGA | (SEQ ID NO: 115) | 132302898-132302875 | 823 bp |
| AAAAGAAGCTGAATTTGCTTTAAAAT | (SEQ ID NO: 116) | 132302086-132302101 | |

TABLE 2-continued

Primers used to prepare templates for sequencing

| Primer sequences (forward and reverse) | | Position according to the coordinate system. | PCR product size |
|---|---|---|---|
| AGCAGGATACTGACAGGCAAA | (SEQ ID NO: 117) | 132302324-132302304 | 839 bp |
| TCATTTAAAAATAAATCCCTCTGGA | (SEQ ID NO: 118) | 132301486-132301510 | |
| TGTTTTCCATTTTTCAATCCAA | (SEQ ID NO: 119) | 132301639-132301618 | 772 bp |
| CCAGGGTCCCATTCCTAGTT | (SEQ ID NO: 120) | 132300868-132300887 | |
| GAGGCTTGTGGAGCATTAGC | (SEQ ID NO: 121) | 132301074-132301055 | 829 bp |
| AGCATGGGTTTCCATAGCAG | (SEQ ID NO: 122) | 132300246-132300265 | |
| TGTTTGGGATTGAGGTCCTT | (SEQ ID NO: 123) | 132300436-132300417 | 812 bp |
| TGTGCAGTTCAAACCCATGT | (SEQ ID NO: 124) | 132299625-132299644 | |
| TGTGGTATTGGGTTGCCATT | (SEQ ID NO: 125) | 132299746-132299727 | 843 bp |
| TTCTCCCTACAGGTCCCAGA | (SEQ ID NO: 126) | 132298904-132298923 | |

TABLE 3

Primers for genotyping by restriction enzyme analysis.

| Polymorphism | Primer sequences (forward and reverse) | Position according to the coordinate system. | PCR product size | Restriction Enzyme | Expected profils |
|---|---|---|---|---|---|
| rs6926879 | ATGCACTACCACACTAGGCTGA (SEQ ID NO: 127) | 132304175-132304154 | 314 bp | BseYI | C/C genotype: 164 + 122 + 28 bp |
| | AGCAGCATGAGACATCAATCAC (SEQ ID NO: 128) | 132303883-132303862 | | | G/G genotype: 192 + 122 bp |
| rs34118837 | ATGCACTACCACACTAGGCTGA (SEQ ID NO: 129) | 132304175-132304154 | 314 bp | BseYI | C/C genotype: 164 + 122 + 28 bp |
| | AGCAGCATGAGACATCAATCAC (SEQ ID NO: 130) | 132303883-132303862 | | | G/G genotype: 192 + 122 bp |
| rs1931003 | TGATTCTTGAAATCAAACCTTGAA (SEQ ID NO: 131) | 132307324-132307301 | 273 bp | NlaIII | G/G genotype: 273 bp |
| | GCTAGTAGGTTCCTCAGCAAGG (SEQ ID NO: 132) | 132307073-132307052 | | | A/A genotype: 170 + 103 bp |
| rs12191459 | ATGGCAATGCACACTTTCAC (SEQ ID NO: 133) | 132309590-132309571 | 243 bp | BveI | C/C genotype: 150 + 93 bp |
| | GCTTTGTTGGAGTGCTAGGC (SEQ ID NO: 134) | 132309367-132309348 | | | T/T genotype: 243 bp |
| rs12206863 | CTTGCAGGCATACACACCAC (SEQ ID NO: 135) | 132310798-132310817 | 162 bp | BsmAI | A/A genotype: 107 + 55 bp |
| | AACGGCCAGAGAGGTACAAA (SEQ ID NO: 136) | 132310656-132310637 | | | C/C genotype: 88 + 55 + 19 bp |
| rs7768619 | TGAGAGCCACTGAAGAATGG (SEQ ID NO: 137) | 132319120-132319101 | 224 bp | KspAI | T/T genotype: 224 bp |
| | TAGGTGGAGCCTAGGGGACT (SEQ ID NO: 138) | 132318916-132318897 | | | C/C genotype: 127 + 97 bp |
| rs10872386 | GGGGACATTTTCCAGACACA (SEQ ID NO: 139) | 132323619-132323600 | 229 bp | BanI | C/C genotype: 102 + 74 + 63 bp |
| | TGTCATCAAATTGCCACAGG (SEQ ID NO: 140) | 132323410-132323391 | | | T/T genotype: 165 + 74 bp |
| rs2327184 | AGCGAGACTCCGTCTCAAAA (SEQ ID NO: 141) | 132324882-132324863 | 225 bp | BsuRI | A/A genotype: 225 bp |
| | CTTTGCTTTCCGCTGTGATT (SEQ ID NO: 142) | 132324677-132324658 | | | G/G genotype: 164 + 61 bp |

EXAMPLES

Example 1

Association Between SNPs in the CTGF Gene Locus with Severe Hepatic Fibrosis (HF) in Two Chinese Populations' Samples

Data are provided for two independent Chinese samples (fishermen and farmers living in region endemic for *S. japonicum*). Disease phenotype included advanced hepatic fibrosis (fishermen) as described in Materials and Methods, or ascites and previous bleedings (farmers).

Association between genotypes and hepatic fibrosis (HF) phenotypes (described in Material and Methods) have been tested first using univariate analysis (upper part of the Table 4) and second by multivariate analysis (lower part of the Table 4) including SNPs or alterations rs12526196, rs1931002, rs3037970 and rs9402373 that showed the strongest associations when tested again SNPs from the same bin. Bins are correlation ($r2>0.5$) groups, genotype is the aggravating genotype, OR=Odd ratios, CI=Confidence interval of OR.

Fisherman sample: n=300, 99 cases and 201 controls; covariates: number of years fishing, being born on boat, gender, number of Praziquantel treatments. Chinese farmer sample: n=294, 113 controls and 181 cases; covariates place of birth is endemic or not endemic, cured or active HBV infection (p=0.05, OR=2.38).

Analysis of the various factors that influence the development of fibrosis in the fishermen population has shown that gender, exposure to infected waters and anti-schistosome treatments with Praziquantel were significantly associated with the risk of fibrosis. The testing of several covariates has shown that "the number of years fishing" and "being born on a fishing boat" were the best covariates to measure exposure. The "treatment" covariate is the number of Praziquantel treatments over the last twenty years.

Study Samples

Chinese fishermen were recruited (fisherman sample) on boats during a large field study, whereas farmers (farmer sample) were recruited from hospital records (cases) directly from their farms or villages (controls). Fishermen live on boat and or on small islands and fish since many years. They were much exposed to infection whereas most farmers have been infected a long time ago since parasite transmission in fields has been interrupted 15 to 20 years ago. Fishermen and farmers originate from different geographical regions. Fishermen are mostly from Jiangshu province and a few of them from Hubei and Jiangxi. Farmers have been living in Hunan province for several generations and for some of them were coming from the mountain area.

Hepatic fibrosis (HF) was evaluated accordingly to the WHO guidelines modified as indicated in (Arnaud et al, 2008). The fisherman sample comprised 300 subjects (201 controls, 99 cases). Cases exhibited either severe CentF (central fibrosis: CLH, D, E or F) or severe ParF (parenchymal fibrosis: GNH or GW) or both CLM and GNM. Controls had milder disease: CentFib≤CLL and ParF≤GNL. Covariates that could affect hepatic fibrosis in fishermen were exposure and the number of Praziquantel treatments. Exposure included two covariates: the number of years fishing and being born on a boat. The Chinese farmer sample included 294 subjects (113 controls and 181 cases). Cases had severe HF (as defined for the fishermen cases) and ascites and/or varicose veins. HBV and HCV infections could be evaluated in this sample; 3 subjects were infected with HCV and were not included, whereas >60% had an active or cured HBV infection. HBV infection was a significant covariate in the analysis (p<0.03), exposure and the number of treatments could not be evaluated accurately in Chinese farmers.

The inventors selected several SNPs for genotyping, two SNPs per bin and any SNPs in or outside the bins that could have a functional effect as determined by in silico analysis (see FIG. 1). These SNPs were then genotyped in a larger cohort of 450 individuals of the Chinese Fisherman cohort.

SNPs showing either positive or suggestive association with fibrosis are presented in Table 4. The correction factor to be applied to these data is <20 (see Materials and Methods). Since treatments could not be recorded accurately for all subjects, we show separately the data obtained with the 450 subjects for whom we knew exposure and with the 380 subjects for whom both exposure and treatments were known.

The inventors have first examined HF in fishermen of the Dong Ting Lake in central China that is highly endemic for *S. japonicum*. Covariates that influenced the development of HF were gender, exposure and anti-schistosome treatments. Using these covariates, we tested on 201 controls and 99 cases whether SNPs (3 SNPs per gene) in CCN2 and IFNGR1 were associated with HF. SNP rs9399005 close to CCN2 showed an association with HF (p=0.02). Sequencing CCN2 (3.2 kb) and 15.3 Kb upstream the starting codon and 14.1 Kb in the 3'UTR region revealed 61 SNPs (FIG. 1) among which 50 had been described before. The 53 SNPs with a MAF>20% were grouped in seven correlation (r2=0.5) bins (I to VII) (FIG. 1). We selected 22 SNPs for further genotyping, at least two SNPs per bin and SNPs (n=4) outside the bins that could have a functional effect as assessed by in silico analysis. SNPs associated with HF (Table 4) were SNP rs12527705 (p=0.02, OR=2.3) and SNP rs12526196 (p=0.02, or =2.2) in bin II, SNP rs9399005 (p=0.02, OR=2.2), SNP rs6918698 (p=0.02, OR=2) and D/I rs3037970 (p=0.003, OR=2.6) in bin III, SNP rs1931002 (p=0.004, OR=2.3) and rs21551532 (p=0.02, OR=1.98) in bin IV and SNP rs9402373 (p=0.015, OR=2) in bin VI. The analysis was adjusted on gender (p<0.001) exposure (fishing years: p<0.001, born on boat: p<0.01) and number of treatments (p<0.01). Deletion/insertion (D/I) rs3037970 excluded rs6918698 in a multivariate analysis testing simultaneously both SNPs. Likewise SNP rs1931002 excluded SNP rs21551532; SNP rs1256196 excluded SNP rs12527705 and SNP rs9399005. This indicated that SNPs rs12526196, rs30337970, rs1931002, rs9402373 had the strongest association with HF. When all four SNPs were tested in the same regression model (lower part Table 4), SNPs rs12526196 (p=0.007, OR=3), rs9402373 (p=0.002, OR=2.8) and rs1931002 (p=0.002, OR=2.8) showed independent associated with HF. An haplotype 1002C, 6196T, present in 53.9% controls and 67.5 cases was associated with HF (p<0.005). The inventors also tested a phenotype that associated advanced HF with evidence of portal hypertension. They found (154 controls and 151 cases) SNP rs9402373 (p=0.005, OR=2.6) and D/I rs3037970 (p=0.05, OR=2) were associated with that phenotype, SNP rs1256196 showed a trend for an association with this more severe disease phenotype (p=0.12). Gender (p=0.001) entered the model as covariate. This suggested that both rs9402373 and D/I rs3037970 could have a more important contribution to severe fibrosis.

The inventors sought replication of these results in an additional independent sample of Chinese farmers who were infected by *S. japonicum* while working in fields and were recruited from the records of local hospitals. The SNPs that had showed some evidence of an association with HF in the fisherman sample were genotyped in the farmer sample (113 controls, 181 cases). An univariate analysis showed associations between severe HF and SNP rs9402373 (p=0.003, OR=2.23) and SNP rs1256196 (p=0.02, OR=1.85). Other SNPs were not associated (p>0.1). Multivariate analysis indicated that both SNPs rs9402373 (p=0.03, OR=2.26) and rs1256196 (p=0.02, OR=1.88) were independently associated with severe fibrosis. Covariates were birth place (endemic or not endemic, p=0.03) and infection with HVB (p=0.05).

zilians than in the Chinese and Sudanese. Severe HF with portal hypertension was observed in less than 2% of the population. All subjects showing clear evidence of periportal thickening of the secondary portal branches were cases, whereas the other subjects with similar contacts with the river were controls.

The inventors have investigated whether hepatic fibrosis in Brazilians infected with *S. mansoni* is also affected by CTGF

TABLE 4

| | | | | Chinese samples | | | | | | | | | |
|---|---|---|---|---|---|---|---|---|---|---|---|---|---|
| SNP or alteration | Position | Bins | Genotype | Controls % | Cases % | OR | 95% CI | p | Controls % | Cases % | OR | 95% CI | p |
| | | | | Chinese Fishermen | | | | | Chinese Farmers | | | | |
| 12527705 | 132304944 | II | AA | 69.1 | 83.7 | 2.26 | 1.13-4.5 | 0.02 | 65.1 | 72 | 1.67 | 0.98-2.84 | 0.06 |
| 12526196 | 132305169 | II | TT | 67.9 | 82.5 | 2.21 | 1.13-4.4 | 0.02 | 61.6 | 71.8 | 1.85 | 1.1-3.1 | 0.02 |
| 9399005 | 132310657 | III | CC | 17.2 | 26.3 | 2.2 | 1.1-4.29 | 0.02 | | | | | NS |
| 6918698 | 132314950 | III | CC | 26.6 | 35.1 | 2.0 | 1.1-3.7 | 0.02 | | | | | NS |
| 3037970 | 132316891 | III | —/— | 27.3 | 38.8 | 2.59 | 1.4-4.8 | 0.003 | | | | | NS |
| 1931002 | 132320175 | IV | CC | 52.5 | 66.7 | 2.32 | 1.3-4.13 | 0.004 | | | | | NS |
| 21551532 | 132316423 | IV | AA | 55.4 | 65 | 1.98 | 1.12-3.5 | 0.02 | | | | | NS |
| 9402373 | 132319124 | VI | CC | 50.3 | 60.6 | 2.04 | 1.15-3.54 | 0.015 | 25 | 43.1 | 2.23 | 1.32-3.76 | 0.003 |
| 12526196 | | II | TT | | | 3.0 | 1.4-6.6 | 0.007 | | | 1.88 | 1.13-3.19 | 0.018 |
| 9402373 | | VI | CC | | | 2.8 | 1.5-5.4 | 0.002 | | | 2.26 | 1.33-3.83 | 0.03 |
| 1931002 | | IV | CC | | | 2.81 | 1.47-5.37 | 0.002 | | | | | |

Example 2

Association Between SNPs in the CTGF Gene Locus with Severe Hepatic Fibrosis (HF) in Sudaneses and Brazilians Infected with *Schistosoma mansoni*

The two principal schistosome strains that cause HF are *S. japonicum* in Asia, and *S. mansoni* in Africa and in South America. We have investigated whether HF in *S. mansoni* endemic region of Sudan and Brazil was also affected by CTGF allelic variants. CTGF polymorphisms that were associated with HF in Chinese fishermen (Table 4) were genotyped in both samples. The phenotypes were either severe HF associated with portal hypertension in Sudanese or significant secondary portal branch thickening in Brazilians who were much less affected than Sudanese since transmission was lower in the Brazilians than in the Sudanese sample.

Associations between genotypes and HF phenotypes (described in Materials and Methods) have been tested first using univariate analysis (upper part of Table 5) and second by multivariate analysis (lower part of Table 5) including SNPs rs12526196, rs 12527705 and rs9402373. Genotype is the aggravating genotype, OR=Odd ratios, CI=Confidence interval of OR.

Sudanese farmers: 314: 219 controls and 95 cases. Brazilians 133: 60 cases and 73 controls.

Study Samples

The Sudanese sample (314 subjects, 95 cases and 219 controls) was recruited among farmers living in villages of the Wad Medani region of Sudan (Dessein et al., 1999). Severe phenotypes associated HF (grade≤C) with evidence of portal hypertension as in (Dessein et al., 1999). All subjects were much exposed to infection with *S. mansoni* and had received no or few Praziquantel treatments. However, exposure and the number of treatments could not be accurately evaluated on this sample.

The Brazilian sample (133 subjects, 73 controls and 60 cases) was recruited in a village of North East Brazil among adult subjects with frequent contacts with a river populated with *S. mansoni* infested snails. Infection was much less, as assessed by schistosome egg excretion in teenagers, in Braallelic variants. The Brazilian cohort has been recruited for this study and has never been genotyped before. We have genotyped CTGF polymorphisms that yield a clear or a suggestive association with fibrosis in Chinese fishermen. In this association study cases were subjects with evidence of thickening of the wall of the secondary branches of the portal vein. The only confounding variable was age of the patients. All subjects with evidence of exposure to infection for many years were selected.

The inventors have investigated next whether HF caused by *S. mansoni* in endemic subjects in Sudan and Brazil was also affected by CTGF allelic variants. CTGF polymorphisms associated with HF in Chinese fishermen were genotyped in both samples. The phenotypes were either severe HF associated with portal hypertension in Sudanese or significant secondary portal branch thickening in Brazilians who were much less affected than Sudanese.

Conclusions:

Univariate analysis (Table 5 left) in Sudanese (219 controls, 95 cases) showed that SNPs rs9402373 (p=0.02, OR=2.7), rs1256196 (p=0.044, OR=3.2) and rs12527705 (p=0.05, OR=3) were associated with severe HF. The aggravating genotypes were identical in Sudanese and Chinese (Tables 4 and 5). Multivariate analysis indicated SNP rs9402373 (p=0.03, OR=2.7) and SNP rs1256196 (p=0.03, OR=3.5) were independently associated with the HF without additional covariates.

Univariate analysis of the genotyping data of the Brazilians (73 controls, 60 cases) showed (Table 5 right) associations between SNP rs9402373 (p=0.02, OR=2.57) and SNP rs6918698 (p=0.008, OR=3) with HF without additional covariates. The genotypes associated with disease for both SNPs were the same as in Chinese and Sudanese (Tables 4 and 5). Multivariate analysis indicated SNPs rs9402373 and rs6918698 were independently (p<0.001, OR>4) associated with HF in Brazilians.

In silico analysis had suggested that the allelic variants SNPs rs9402373 and rs12526196 might bind differently nuclear factors. We have demonstrated this with EMSA: the rs9402373C allele bound nuclear factors that were not bound by the G allele (FIG. 2A). This binding was competed with specific unbiotinylated probe (FIG. 2B). EMSA also showed a greater binding affinity of nuclear factors to the rs12526196T allele (FIG. 2A). EMSA did not reveal allele specific binding for rs12527705 and rs1931002 polymorphisms (FIG. 2A).

Then SNP rs9402373 was associated with HF in all four samples tested. This association was obtained in Chinese and Sudanese, using a strict fibrosis phenotype or a more severe phenotype (HF+evidence of portal blood hypertension). SNP rs1256196 was also independently associated with HF in Chinese and Sudanese. Our EMSA data indicate that allelic variants of SNP rs1256196 and SNP rs9402373 bind differently nuclear factor suggesting that they could affect the regulation of gene transcription or the stability of transcripts.

HBV infection was a significant covariate in the analysis of Chinese farmers indicating that HBV likely contributed significantly to severe disease. This also suggests that SNP rs1256196 and SNP rs9402373 might also modulate HF caused by HBV.

In conclusion the present study shows the association of polymorphisms with fibrosis, and identifies most critical steps in disease development indicating new therapeutical targets. It also provides valuable markers of HF progression.

fibrosis. The CG and GG genotypes of SNP rs6918698 were associated with disease aggravation (OR=2.1, CI=1.1-4.0).

Bin VI only contains SNP rs9402373 that was also (p=0.007) associated with hepatic fibrosis in the French sample. Disease was aggravated by the CC genotype (OR=2.54; 1.3-4.96). Interestingly, the subjects homozygous C/C showed an average four-fold increase of the risk of severe hepatic fibrosis as compared to homozygous GG (OR=4.1 CI=1.1-14). Multivariate logistic regression analysis that included SNP rs6918698 and SNP rs9402373 indicated that the latter was the most strongly associated with hepatic fibrosis. Nevertheless in the presence of SNP rs9402373, SNP rs6918698 still showed a trend for an association with hepatic disease suggesting that SNP rs9402373 could not account for the full association of SNP rs6918698 with disease. Thus the inventors concluded both SNPs are independently associated with fibrosis.

CTGF Genetic Variants are Also Associated with Hepatic Fibrosis in Brazilians Infected with HCV.

The inventors then sought the confirmation of the above described findings by testing SNPs from the same four bins in Brazilians infected with HCV. They found that SNP rs6918698 (p=0.0004) was clearly associated with hepatic

TABLE 5

| | Sudanese sample | | | | | | Brazilian sample | | | | | | |
|---|---|---|---|---|---|---|---|---|---|---|---|---|---|
| SNP or alteration | Genotype | Controls % | Cases % | OR | 95% CI | P | SNP | Genotype | Controls % | Cases % | OR | 95% CI | P |
| 12527705 | AA | 82.1 | 90.5 | 3 | 1-9.1 | 0.05 | 12527705 | | | | | | NS |
| 12526196 | TT | 80.8 | 90.5 | 3.2 | 1-9.7 | 0.44 | 12526196 | | | | | | NS |
| 3037970 | —/— | | | | | NS | 3037970 | —/— | 80.5 | 90.2 | | | 0.12 |
| 6918698 | CC | | | | | NS | 6918698 | CC + CG | 63 | 83.9 | 3.05 | 1.33-6.98 | 0.008 |
| 9402373 | CC | 80 | 89.8 | 2.75 | 1.17-6.5 | 0.02 | 9402373 | CC | 60.3 | 80.0 | 2.57 | 1.18-5.64 | 0.018 |
| 12526196 | TT | | | 3.5 | 1.1-10.9 | 0.03 | 6918698 | CC | | | 4.92 | 2.0-12 | $5 \times 10^{-4}$ |
| 9402373 | CC | | | 2.76 | 1.2-6.7 | 0.026 | 9402373 | CC | | | 4.25 | 1.79-10.08 | $9 \times 10^{-4}$ |

Example 3

Association Between SNPs in the CTGF Gene Locus with Hepatic Fibrosis (HF) in HCV Infected Subjects Analysis of CTGF Genetic Variants in French Subjects Infected with HCV.

Example 1 describes SNP correlation bins (r2>0.8) in the CTGF encoding gene in a sample of Chinese population. These were defined over the entire gene and 10 Kb of the 3' and 5' flanking region. Only SNPs with a minor allele frequency >20% had been analyzed. There were seven bins of which four (groups II, III, IV and VI) showed some association with hepatic fibrosis caused by schistosome eggs in Chinese fishermen infected by *Schistosoma japonicum*. In Example 3, the inventors genotyped two SNPs in each of these four bins and an additional SNP rs9399005 (that showed suggestive associations with schistosomal fibrosis) in a French sample infected with HCV and determined whether any of them were associated with advanced hepatic fibrosis. They found evidence for association in bins III and VI but not in bins II and IV. SNP rs6918698 (p=0.03) and SNP rs3037970 (p=0.04) in bin IV, were associated with hepatic fibrosis. SNP rs3037970 showed a trend (p=0.07) for an association and SNP rs6918698 accounted for SNP rs3037970 association. The SNP rs6918698 aggravating genotype was G/G (OR 2.94; 1.5-7.7). As in the French sample, the inventors observed that SNP rs9402373 in bin VI, was strongly (p=0.003) associated with hepatic fibrosis (OR=2.94, 1.45-5.97) in the Brazilian sample. Of note, in this sample as in the French sample, C/C aggravated disease. Since subjects carrying the G/G genotype were few, the inventors could not compare the risk of severe fibrosis between homozygous subjects. Finally the inventors also showed a trend (p=0.06) for an association of SNPrs9399005 with hepatic fibrosis.

Logistic regression analysis showed that both SNP rs9402373 (p=0.029) and SNP rs6918698 (p=0.03) contributed independently to hepatic fibrosis with comparable relative risks (OR=2.4-2.5) and that the association of SNP rs9399005 with fibrosis was lost in the presence of the two other SNPs suggesting that the association of this SNP with hepatic fibrosis likely is entirely accounted for by its correlation with SNP rs9402373 and SNP rs6918698. It can not totally be excluded, however, that SNP rs9399005 could also be independently associated with hepatic fibrosis.

TABLE 6

SNPs rs 6918698 and rs9402373 are associated with hepatic fibrosis in HCV infected subjects

| | | | | | French Sample | | | | |
|---|---|---|---|---|---|---|---|---|---|
| Analysis | SNP | Position | Bins | GENOTYPE (aggravating)[2] | CONTROLS % | CASES % | OR | 95% CI | P |
| Univariate | 1257705 | 132304944 | II | | | | | | NS > 1.4 |
| | 12526196 | 132305169 | II | CT* | | | | | NS > 1.3 |
| | 9399005 | 132310657 | | CC | | | | | NS > 0.3 |
| | 3037970 | 132316891 | III | Del, del (French) Del, del, del/wt (Brazilians) | 67.8 (78) | 79.5 (89) | 1.9 | 1.03-3.6 | 0.04 |
| | 6918698 | 132314950 | III | GG + CG (French) GG (Brazilians) | 68.4 (78) | 81.7 (89)) | 2.1 | 1.1-4 | 0.025 |
| | 1931002 | 132320175 | IV | | | | | | NS > 0.5 |
| | 2151532 | 132316423 | IV | | | | | | NS > 0.5 |
| | 9402373 | 132319124 | VI | CC | 51.3 (61) | 70.8 (46) | 2.54 | 1.3-4.96 | 0.007 |
| | 12527379 | | | AG + AA | 57.1 (64) | 67 (69) | 1.7 | 0.94-2.97 | 0.08 |
| Multivariate | 6918698 | | | C/G + G/G (french) G/G (Brazilians) | | | 1.54 | 0.77-3.1 | 0.22 |
| | 9402373 | | | C/C | | | 2.1 | 1.15-4 | 0.017 |

| | | | | | Brazilian Sample | | | | |
|---|---|---|---|---|---|---|---|---|---|
| Analysis | SNP | Position | Bins | GENOTYPE (aggravating)[2] | CONTROLS % | CASES % | OR | 95% CI | P |
| Univariate | 1257705 | 132304944 | II | | | | | | NS > 1.4 |
| | 12526196 | 132305169 | II | CT* | | | | | NS > 1.3 |
| | 9399005 | 132310657 | | CC | 57.4 (39) | 72.4 (92) | 1.9 | 0.97-3.7 | 0.06 |
| | 3037970 | 132316891 | III | Del, del (French) Del, del, del/wt (Brazilians) | 61 (41) | 75 (93) | 1.9 | 0.95-3.9 | 0.07 |
| | 6918698 | 132314950 | III | GG + CG (French) GG (Brazilians) | 16.4 (11) | 34.4 (44) | 3.3 | 1.5-7.7 | 0.004 |
| | 1931002 | 132320175 | IV | | | | | | NS > 0.2 |
| | 2151532 | 132316423 | IV | | | | | | NS > 0.2 |
| | 9402373 | 132319124 | VI | CC | 58.8 (40) | 79.7 (102) | 2.5 | 1.1-5 | 0.003 |
| | 12527379 | | | AG + AA | 38.2 (26) | 50.0 (64) | 1.8 | 0.94-3.5 | .08 |
| Multivariate | 6918698 | | | C/G + G/G (french) G/G (Brazilians) | | | 2.5 | 1.1-5.9 | 0.03 |
| | 9402373 | | | C/C | | | 2.4 | 1.1-5 | 0.029 |

French (n = 222) and Brazilians (n = 196) cohorts, infected with HCV: Covariates Sexe $p < 10^{-3}$ The inventors then performed a Meta analysis of the data obtained with SNP rs9402373 in French and Brazilians infected with HCV.

Such an analysis was not performed with SNP rs6918698 because the fibrosis associated genotypes were different in French (G/G+C/G) and in Brazilians (G/G). The inventors found that SNP rs9402373 CC genotype was associated (p=0.00005, OR=2.72; 1.67-4.43) with hepatic fibrosis caused by HCV.

Since the association of this same CC genotype of SNP rs9402373 was shown with hepatic fibrosis in the above examples, the inventors also performed a Meta analysis of the studies testing the association of this SNP with HCV induced HF (two studies) and schistosomal induced HF (4 studies). The results of such a Meta analysis are presented in FIG. 3 and show that CC of the SNP rs9402373 is strongly associated (p<10-9) with severe hepatic fibrosis (OR=2.47; 1.8-3.25) caused by different pathogens HCV, *S. mansoni* and *S. japonicum*) in populations (Chinese, Sudanese, Brazilian and French) with markedly different genetic background.

REFERENCES

Bedossa P., Poynard, T. The METAVIR cooperative study group. An algorithm for the grading of activity in chronic hepatitis C, Hepatology 1996; 24:289-293.

Garcia-Tsao G. Boyer J L. Outpatient liver biopsy: how safe is it? Ann Intern Med 1993; 118: 150-3.

Sebastiani G, Vario A, Guido M et al. Stepwise combination algorithms of non-invasive markers to diagnose significant fibrosis in chronic hepatitis C. J Hepatol 2006; 44: 686-693.

Parkes J, Guha I N, Roderick P et al. Performance of serum marker panels for liver fibrosis in hepatitis C. J Hepatol 2006; 44: 462-474.

Ziol M, et al. Noninvasive assessment of liver fibrosis by measurement of stiffness in patients with chronic hepatitis C. Hepatology 2005; 41:48-54.

Czaja A, Freese D K. Diagnosis and Treatment of Autoimmune hepatitis. Hepatology 2003; 473-496.

Poupon R E, Lindor K D, Cauch-Dudek K, et al. Combined analysis of randomized controlled trials of ursodeoxycholic acid in primary biliary cirrhosis. Gastroenterology 1997; 113:884.

Bruck R, Shirin H, Hershkoviz R, et al. Analysis of Arg-Gly-Asp mimetics and soluble receptor of tumour necrosis factor as therapeutic modalities for concanavalin A induced hepatitis in mice. Gut 1997; 40:133.

Poynard T, Marcellin P, Lee S S, et al. Randomised trial of interferon alpha2b plus ribavirin for 48 weeks or for 24 weeks versus interferon alpha2b plus placebo for 48 weeks for treatment of chronic infection with hepatitis C virus. International Hepatitis Interventional Therapy Group (IHIT). Lancet 1998; 352:1426.

Jonsson J R, Clouston A D, Ando Y, et al. Angiotensin-converting enzyme inhibition attenuates the progression of rat hepatic fibrosis. Gastroenterology 2001; 121:148.

Gressner A M. The cell biology of liver fibrogenesis—an imbalance of proliferation, growth arrest and apoptosis of myofibroblasts. Cell Tissue Res 1998; 292:447.

Dessein, A. J., D. Hillaire, N. E. Elwali, S. Marquet, Q. Mohamed-Ali, A. Mirghani, S. Henri, A. A. Abdelhameed, O. K. Saeed, M. M. Magzoub, and L. Abel. 1999. Severe hepatic fibrosis in *Schistosoma mansoni* infection is controlled by a major locus that is closely linked to the interferon-gamma receptor gene. Am J Hum Genet 65:709.

Kobayashi, H., N. Hayashi, K. Hayashi, A. Yamataka, G. J. Lane, and T. Miyano. 2005. Connective tissue growth factor and progressive fibrosis in biliary atresia. Pediatr Surg Int 21:12.

Gressner, O. A., B. Lahme, I. Demirci, A. M. Gressner, and R. Weiskirchen. 2007. Differential effects of TGF-beta on connective tissue growth factor (CTGF/CCN2) expression in hepatic stellate cells and hepatocytes. J Hepatol 47:699.

Gressner, O. A., and A. M. Gressner. 2008. Connective tissue growth factor: a fibrogenic master switch in fibrotic liver diseases. Liver Int 28:1065.

Fonseca, C., G. E. Lindahl, M. Ponticos, P. Sestini, E. A. Renzoni, A. M. Holmes, P. Spagnolo, P. Pantelidis, P. Leoni, N. McHugh, C. J. Stock, X. Shi-Wen, C. P. Denton, C. M. Black, K. I. Welsh, R. M. du Bois, and D. J. Abraham. 2007. A polymorphism in the CTGF promoter region associated with systemic sclerosis. N Engl J Med 357:1210.

Gourh, P., M. D. Mayes, and F. C. Arnett. 2008. CTGF polymorphism associated with systemic sclerosis. N Engl J Med 358:308.

Morita, H., D. Hayashi, and R. Nagai. 2008. CTGF polymorphism associated with systemic sclerosis. N Engl J Med 358:308; author reply 309.

Ivkovic, S., B. S. Yoon, S. N. Popoff, F. F. Safadi, D. E. Libuda, R. C. Stephenson, A. Daluiski, and K. M. Lyons. 2003. Connective tissue growth factor coordinates chondrogenesis and angiogenesis during skeletal development. Development 130:2779.

Leask, A., and D. J. Abraham. 2006. All in the CCN family: essential matricellular signaling modulators emerge from the bunker. J Cell Sci 119:4803.

Leask, A., and D. J. Abraham. 2003. The role of connective tissue growth factor, a multifunctional matricellular protein, in fibroblast biology. Biochem Cell Biol 81:355.

Wahab, N. A., B. S. Weston, and R. M. Mason. 2005. Modulation of the TGFbeta/Smad signaling pathway in mesangial cells by CTGF/CCN2. Exp Cell Res 307:305.

Abreu, J. G., N. I. Ketpura, B. Reversade, and E. M. De Robertis. 2002. Connective-tissue growth factor (CTGF) modulates cell signalling by BMP and TGF-beta. Nat Cell Biol 4:599.

Kalluri, R., and E. G. Neilson. 2003. Epithelial-mesenchymal transition and its implications for fibrosis. J Clin Invest 112:1776.

Neilson, E. G. 2005. Setting a trap for tissue fibrosis. Nat Med 11:373.

Yoshida, K., and H. Munakata. 2007. Connective tissue growth factor binds to fibronectin through the type I repeat modules and enhances the affinity of fibronectin to fibrin. Biochim Biophys Acta 1770:672.

Rachfal, A. W., and D. R. Brigstock. 2003. Connective tissue growth factor (CTGF/CCN2) in hepatic fibrosis. Hepatol Res 26:1.

Li, G., Q. Xie, Y. Shi, D. Li, M. Zhang, S. Jiang, H. Zhou, H. Lu, and Y. Jin. 2006. Inhibition of connective tissue growth factor by siRNA prevents liver fibrosis in rats. J Gene Med 8:889.

George, J., and M. Tsutsumi. 2007. siRNA-mediated knock-down of connective tissue growth factor prevents N-nitrosodimethylamine-induced hepatic fibrosis in rats. Gene Ther 14:790.

Brigstock, D. R. 2002. Regulation of angiogenesis and endothelial cell function by connective tissue growth factor (CTGF) and cysteine-rich 61 (CYR61). Angiogenesis 5:153.

Shimo, T., T. Nakanishi, T. Nishida, M. Asano, A. Sasaki, M. Kanyama, T. Kuboki, T. Matsumura, and M. Takigawa. 2001. Involvement of CTGF, a hypertrophic chondrocyte-specific gene product, in tumor angiogenesis. Oncology 61:315.

Gao, R., D. K. Ball, B. Perbal, and D. R. Brigstock. 2004. Connective tissue growth factor induces c-fos gene activation and cell proliferation through p44/42 MAP kinase in primary rat hepatic stellate cells. J Hepatol 40:431.

Croci, S., L. Landuzzi, A. Astolfi, G. Nicoletti, A. Rosolen, F. Sartori, M. Y. Follo, N. Oliver, C. De Giovanni, P. Nanni, and P. L. Lollini. 2004. Inhibition of connective tissue growth factor (CTGF/CCN2) expression decreases the survival and myogenic differentiation of human rhabdomyosarcoma cells. Cancer Res 64:1730.

Henri, S., C. Chevillard, A. Mergani, P. Paris, J. Gaudart, C. Camilla, H. Dessein, F. Montero, N. E. Elwali, O. K. Saeed, M. Magzoub, and A. J. Dessein. 2002. Cytokine regulation of periportal fibrosis in humans infected with *Schistosoma mansoni*: IFN-gamma is associated with protection against fibrosis and TNF-alpha with aggravation of disease. J Immunol 169:929.

Chevillard, C., C. E. Moukoko, N. E. Elwali, J. H. Bream, B. Kouriba, L. Argiro, S. Rahoud, A. Mergani, S. Henri, J. Gaudart, Q. Mohamed-Ali, H. A. Young, and A. J. Dessein. 2003. IFN-gamma polymorphisms (IFN-gamma +2109 and IFN-gamma +3810) are associated with severe hepatic fibrosis in human hepatic schistosomiasis (*Schistosoma mansoni*). J Immunol 171:5596.

Fitzner, B., P. Brock, H. Nechutova, A. Glass, T. Karopka, D. Koczan, H. J. Thiesen, G. Sparmann, J. Emmrich, S. Liebe, and R. Jaster. 2007. Inhibitory effects of interferon-gamma on activation of rat pancreatic stellate cells are mediated by STAT1 and involve down-regulation of CTGF expression. Cell Signal 19:782.

Li, J., and L. Ji. 2005. Adjusting multiple testing in multilocus analyses using the eigenvalues of a correlation matrix. Heredity 95:221.

Nyholt, D. R. 2004. A simple correction for multiple testing for single-nucleotide polymorphisms in linkage disequilibrium with each other. Am J Hum Genet 74:765.

Mohamed-Ali Q, Elwali N E, Abdelhameed A A, Mergani A, Rahoud S, Elagib K E, Saeed O K, Abel L, Magzoub M M, Dessein A J. Susceptibility to periportal (Symmers) fibrosis in human *schistosoma mansoni* infections: evidence that intensity and duration of infection, gender, and inherited factors are critical in disease progression. J Infect Dis. 1999 October; 180(4):1298-306. PMID: 10479161

Boursier J, Konaté A, Gorea G, Reaud S, Quemener E, Oberti F, Hubert-Fouchard I, Dib N, Calès P. Reproducibility of liver stiffness measurement by ultrasonographic elastometry. Clin Gastroenterol Hepatol. 2008 November; 6(11): 1263-9. Epub 2008 Aug. 30. PMID: 18995217.

Macías J, Recio E, Vispo E, Rivero A, López-Cortés L F, Ríos M J, Merino D, González M, Barreiro P, de Lédinghen V, Quereda C, Pineda J A. Application of transient elastometry to differentiate mild from moderate to severe liver fibrosis in HIV/HCV co-infected patients. J. Hepatol. 2008 December; 49(6):916-22. Epub 2008 Oct. 1.

Richter J, Domingues A L, Barata C H, Prata A R, Lambertucci J R. Report of the second satellite symposium on ultrasound in schistosomiasis. Mem Inst Oswaldo Cruz. 2001; 96 Suppl:151-6. PMID: 11586442

Lambertucci J R, Silva L C, Andrade L M, de Queiroz L C, Pinto-Silva R A. Magnetic resonance imaging and ultrasound in hepatosplenic schistosomiasis mansoni. Rev Soc Bras Med Trop. 2004 July August; 37(4):333-7. Epub 2004 Aug. 20. PMID: 15334268

King C H, Magak P, Salam E A, Ouma J H, Kariuki H C, Blanton R E; World Health Organization. Measuring morbidity in schistosomiasis mansoni: relationship between image pattern, portal vein diameter and portal branch thickness in large-scale surveys using new WHO coding guidelines for ultrasound in schistosomiasis. Trop Med Int Health. 2003 February; 8(2):109-17. PMID: 12581434

Arnaud, V., J. Li, Y. Wang, X. Fu, S. Mengzhi, X. Luo, X. Hou, H. Dessein, Z. Jie, Y. Xin-Ling, H. He, D. P. McManus, Y. Li, and A. Dessein. 2008. Regulatory role of interleukin-10 and interferon-gamma in severe hepatic central and peripheral fibrosis in humans infected with *Schistosoma japonicum*. *J Infect Dis* 198:418.

The invention claimed is:

1. A method for determining an increased risk of hepatic fibrosis in a human subject, the method comprising:
   (a) obtaining a sample from the human subject;
   (b) detecting a CC genotype at rs9402373 in the sample using a probe consisting of SEQ ID NO: 33 or SEQ ID NO: 34; and
   (c) identifying the human subject having a CC genotype at rs9402373 as having an increased risk of hepatic fibrosis as compared to a human subject having a GG genotype at rs9402373.

2. The method of claim 1, wherein the hepatic fibrosis is caused by hepatitis A virus infection.

3. The method of claim 1, wherein the hepatic fibrosis is caused by hepatitis B virus infection.

4. The method of claim 1, wherein the hepatic fibrosis is caused by hepatitis C virus infection.

5. The method of claim 1, wherein the hepatic fibrosis is caused by *Schistosoma japonicum* infection.

6. The method of claim 1, wherein the hepatic fibrosis is caused by *Schistosoma mansoni* infection.

7. A method of determining whether a subject is a candidate for a treatment for hepatic fibrosis, the method comprising:
   (a) obtaining a sample from a human subject;
   (b) detecting a CC genotype at rs9402373 in the sample using a probe consisting of SEQ ID NO: 33 or SEQ ID NO: 34;
   (c) identifying the human subject having a CC genotype at rs9402373 as having an increased risk for hepatic fibrosis as compared to a human subject having a GG genotype at rs9402373; and
   (d) determining that the subject with a CC genotype is a candidate for the treatment for hepatic fibrosis.

8. The method of claim 7, wherein the hepatic fibrosis is caused by hepatitis A virus infection.

9. The method of claim 7, wherein the hepatic fibrosis is caused by hepatitis B virus infection.

10. The method of claim 7, wherein the hepatic fibrosis is caused by hepatitis C virus infection.

11. The method of claim 7, wherein the hepatic fibrosis is caused by *Schistosoma japonicum* infection.

12. The method of claim 7, wherein the hepatic fibrosis is caused by *Schistosoma mansoni* infection.

13. A method for determining an increased risk of hepatic fibrosis in a human subject, the method comprising:
    (a) obtaining a sample from the human subject;
    (b) detecting a CC genotype at rs9402373 in the sample using a fluorescently labeled probe consisting of SEQ ID NO: 33 or SEQ ID NO: 34; and
    (c) identifying the human subject having a CC genotype at rs9402373 as having an increased risk of hepatic fibrosis as compared to a human subject having a GG genotype at rs9402373.

14. The method of claim 13, wherein the hepatic fibrosis is caused by hepatitis A virus infection.

15. The method of claim 13, wherein the hepatic fibrosis is caused by hepatitis B virus infection.

16. The method of claim 13, wherein the hepatic fibrosis is caused by hepatitis C virus infection.

17. The method of claim 13, wherein the hepatic fibrosis is caused by *Schistosoma japonicum* infection.

18. The method of claim 13, wherein the hepatic fibrosis is caused by *Schistosoma mansoni* infection.

* * * * *